United States Patent
Budiman et al.

(10) Patent No.: US 11,717,225 B2
(45) Date of Patent: Aug. 8, 2023

(54) METHOD AND APPARATUS FOR DETERMINING MEAL START AND PEAK EVENTS IN ANALYTE MONITORING SYSTEMS

(71) Applicant: ABBOTT DIABETES CARE INC., Alameda, CA (US)

(72) Inventors: Erwin Satrya Budiman, Fremont, CA (US); Gary Alan Hayter, Oakland, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 589 days.

(21) Appl. No.: 16/703,196

(22) Filed: Dec. 4, 2019

(65) Prior Publication Data

US 2020/0105397 A1    Apr. 2, 2020

Related U.S. Application Data

(63) Continuation of application No. 15/300,711, filed as application No. PCT/US2015/023380 on Mar. 30, 2015, now abandoned.

(60) Provisional application No. 61/972,381, filed on Mar. 30, 2014.

(51) Int. Cl.
| | |
|---|---|
| *A61B 5/145* | (2006.01) |
| *A61B 5/00* | (2006.01) |
| *G16H 50/20* | (2018.01) |
| *G16H 20/60* | (2018.01) |

(52) U.S. Cl.
CPC ............ *A61B 5/7203* (2013.01); *A61B 5/145* (2013.01); *A61B 5/14532* (2013.01); *A61B 5/7282* (2013.01); *G16H 20/60* (2018.01); *G16H 50/20* (2018.01)

(58) Field of Classification Search
CPC ... A61B 5/7203; A61B 5/145; A61B 5/14532; A61B 5/7282; G16H 50/20; G16H 20/60
See application file for complete search history.

(56) References Cited

U.S. PATENT DOCUMENTS

| | | | |
|---|---|---|---|
| 3,581,062 | A | 5/1971 | Aston |
| 3,926,760 | A | 12/1975 | Allen et al. |
| 3,949,388 | A | 4/1976 | Fuller |
| 3,960,497 | A | 6/1976 | Acord et al. |
| 3,978,856 | A | 9/1976 | Michel |
| 4,036,749 | A | 7/1977 | Anderson |

(Continued)

FOREIGN PATENT DOCUMENTS

| | | |
|---|---|---|
| EP | 0098592 | 1/1984 |
| EP | 0127958 | 12/1984 |

(Continued)

OTHER PUBLICATIONS

Armour, J. C., et al., "Application of Chronic Intravascular Blood Glucose Sensor in Dogs", Diabetes, vol. 39, 1990, pp. 1519-1526.

(Continued)

*Primary Examiner* — Shirley X Jian
(74) *Attorney, Agent, or Firm* — One LLP

(57) ABSTRACT

Systems, methods and apparatus are provided for estimating meal start and peak meal response times are provided based on time series of sampled glucose data collected. Numerous additional aspects are disclosed.

20 Claims, 10 Drawing Sheets

(56) References Cited

U.S. PATENT DOCUMENTS

| | | |
|---|---|---|
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,532,686 A | 7/1996 | Urbas et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Carter et al. |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,720,295 A | 2/1998 | Greenhut et al. |
| 5,724,030 A | 3/1998 | Urbas et al. |
| 5,733,259 A | 3/1998 | Valcke et al. |
| 5,735,285 A | 4/1998 | Albert et al. |
| 5,741,211 A | 4/1998 | Renirie et al. |
| 5,749,907 A | 5/1998 | Mann |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,804,047 A | 9/1998 | Karube et al. |
| 5,820,551 A | 10/1998 | Hill et al. |
| 5,822,715 A | 10/1998 | Worthington et al. |
| 5,891,047 A | 4/1999 | Lander et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |

(56) References Cited

U.S. PATENT DOCUMENTS

| | | | |
|---|---|---|---|
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,130,623 A | 10/2000 | MacLellan et al. |
| 6,134,461 A | 10/2000 | Say et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,804,558 B2 | 10/2004 | Haller et al. |

(56) References Cited

U.S. PATENT DOCUMENTS

| | | |
|---|---|---|
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,225,535 B2 | 6/2007 | Feldman et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,524,287 B2 | 4/2009 | Bharmi |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,493 B2 | 5/2010 | Bartkowiak et al. |
| 7,736,310 B2 | 6/2010 | Taub et al. |
| 7,741,734 B2 | 6/2010 | Joannopoulos et al. |
| 7,751,864 B2 | 7/2010 | Buck, Jr. |
| 7,766,829 B2 | 8/2010 | Sloan et al. |

(56) References Cited

U.S. PATENT DOCUMENTS

| | | |
|---|---|---|
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,826,981 B2 | 11/2010 | Goode, Jr. et al. |
| 7,831,310 B2 | 11/2010 | Lebel et al. |
| 7,857,760 B2 | 12/2010 | Brister et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,938,797 B2 | 5/2011 | Estes |
| 7,946,984 B2 | 5/2011 | Brister et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,116,837 B2 | 2/2012 | Huang |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,900 B2 | 4/2012 | Taub et al. |
| 8,170,803 B2 | 5/2012 | Kamath et al. |
| 8,179,266 B2 | 5/2012 | Hermle |
| 8,216,138 B1 | 7/2012 | McGarraugh et al. |
| 8,224,415 B2 | 7/2012 | Budiman et al. |
| 8,231,531 B2 | 7/2012 | Brister et al. |
| 8,239,166 B2 | 8/2012 | Hayter et al. |
| 8,255,026 B1 | 8/2012 | Al-Ali |
| 8,282,549 B2 | 10/2012 | Brauker et al. |
| 8,376,945 B2 | 2/2013 | Hayter et al. |
| 8,444,560 B2 | 5/2013 | Hayter et al. |
| 8,457,703 B2 | 6/2013 | Al-Ali |
| 8,484,005 B2 | 7/2013 | Hayter et al. |
| 8,532,935 B2 | 9/2013 | Budiman |
| 8,543,354 B2 | 9/2013 | Luo et al. |
| 8,571,808 B2 | 10/2013 | Hayter |
| 8,612,163 B2 | 12/2013 | Hayter et al. |
| 8,657,746 B2 | 2/2014 | Roy |
| 8,682,615 B2 | 3/2014 | Hayter et al. |
| 9,060,719 B2 | 6/2015 | Hayter et al. |
| 9,398,872 B2 | 7/2016 | Hayter et al. |
| 9,408,566 B2 | 8/2016 | Hayter et al. |
| 9,483,608 B2 | 11/2016 | Hayter et al. |
| 9,558,325 B2 | 1/2017 | Hayter et al. |
| 2001/0041831 A1 | 11/2001 | Starkweather et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0065454 A1 | 5/2002 | Lebel et al. |
| 2002/0068860 A1 | 6/2002 | Clark |
| 2002/0072784 A1 | 6/2002 | Sheppard et al. |
| 2002/0103499 A1 | 8/2002 | Perez et al. |
| 2002/0106709 A1 | 8/2002 | Potts et al. |
| 2002/0120186 A1 | 8/2002 | Keimel |
| 2002/0128594 A1 | 9/2002 | Das et al. |
| 2002/0143266 A1 | 10/2002 | Bock |
| 2002/0143372 A1 | 10/2002 | Snell et al. |
| 2002/0161288 A1 | 10/2002 | Shin et al. |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0065308 A1 | 4/2003 | Lebel et al. |
| 2003/0088166 A1 | 5/2003 | Say et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0142403 A1 | 7/2004 | Hetzel et al. |
| 2004/0146909 A1 | 7/2004 | Duong et al. |
| 2004/0152622 A1 | 8/2004 | Keith et al. |
| 2004/0162678 A1 | 8/2004 | Hetzel et al. |

(56) References Cited

U.S. PATENT DOCUMENTS

| | | |
|---|---|---|
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0115832 A1 | 6/2005 | Simpson et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0091006 A1 | 5/2006 | Wang et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |

(56) References Cited

U.S. PATENT DOCUMENTS

| | | |
|---|---|---|
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0119705 A1 | 5/2008 | Patel et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1* | 2/2009 | Jennewine ......... A61B 5/14532 600/315 |
| 2009/0054748 A1 | 2/2009 | Feldman et al. |

(56) References Cited

U.S. PATENT DOCUMENTS

| | | |
|---|---|---|
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0064764 A1 | 3/2010 | Hayter et al. |
| 2010/0081906 A1 | 4/2010 | Hayter et al. |
| 2010/0081909 A1 | 4/2010 | Budiman et al. |
| 2010/0081953 A1 | 4/2010 | Syeda-Mahmood et al. |
| 2010/0121167 A1 | 5/2010 | McGarraugh et al. |
| 2010/0141656 A1 | 6/2010 | Krieftewirth |
| 2010/0160759 A1 | 6/2010 | Celentano et al. |
| 2010/0160761 A1 | 6/2010 | Say et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0190435 A1 | 7/2010 | Cook et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0230285 A1 | 9/2010 | Hoss et al. |
| 2010/0234710 A1 | 9/2010 | Budiman et al. |
| 2010/0265073 A1 | 10/2010 | Harper et al. |
| 2010/0274515 A1 | 10/2010 | Hoss et al. |
| 2010/0277342 A1 | 11/2010 | Sicurello et al. |
| 2010/0280441 A1 | 11/2010 | Willinska et al. |
| 2010/0280782 A1 | 11/2010 | Harper et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2011/0004276 A1 | 1/2011 | Blair et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0040163 A1 | 2/2011 | Telson et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0082484 A1 | 4/2011 | Saravia et al. |
| 2011/0105873 A1 | 5/2011 | Feldman et al. |
| 2011/0106126 A1 | 5/2011 | Love et al. |
| 2011/0112696 A1 | 5/2011 | Yodfat et al. |
| 2011/0148905 A1 | 6/2011 | Simmons et al. |
| 2011/0152637 A1 | 6/2011 | Kateraas et al. |
| 2011/0184268 A1 | 7/2011 | Taub |
| 2011/0190603 A1 | 8/2011 | Stafford |
| 2011/0191044 A1 | 8/2011 | Stafford |
| 2011/0193704 A1 | 8/2011 | Harper et al. |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0224523 A1 | 9/2011 | Budiman |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0288574 A1 | 11/2011 | Curry et al. |
| 2011/0319729 A1 | 12/2011 | Donnay et al. |
| 2011/0320130 A1 | 12/2011 | Valdes et al. |
| 2011/0320167 A1 | 12/2011 | Budiman |
| 2012/0010642 A1 | 1/2012 | Lee et al. |
| 2012/0078071 A1 | 3/2012 | Bohm et al. |
| 2012/0108931 A1 | 5/2012 | Taub |
| 2012/0108934 A1 | 5/2012 | Valdes et al. |
| 2012/0165626 A1 | 6/2012 | Irina et al. |

(56) References Cited

U.S. PATENT DOCUMENTS

| | | | |
|---|---|---|---|
| 2012/0165640 | A1 | 6/2012 | Galley et al. |
| 2012/0173200 | A1 | 7/2012 | Breton et al. |
| 2012/0209099 | A1 | 8/2012 | Ljuhs et al. |
| 2012/0215462 | A1 | 8/2012 | Goode et al. |
| 2012/0245447 | A1 | 9/2012 | Karan et al. |
| 2013/0035575 | A1 | 2/2013 | Mayou et al. |
| 2013/0184547 | A1 | 7/2013 | Taub et al. |
| 2013/0231541 | A1 | 9/2013 | Hayter et al. |
| 2014/0121480 | A1 | 5/2014 | Budiman et al. |
| 2014/0121488 | A1 | 5/2014 | Budiman |
| 2014/0221966 | A1 | 8/2014 | Buckingham et al. |
| 2015/0216456 | A1 | 8/2015 | Budiman |
| 2015/0241407 | A1 | 8/2015 | Ou et al. |
| 2016/0022221 | A1 | 1/2016 | Ou et al. |
| 2017/0185748 | A1* | 6/2017 | Budiman ............... G16H 50/20 |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1419731 | 5/2004 |
| EP | 0939602 | 9/2004 |
| EP | 1850909 | 4/2010 |
| EP | 1677668 | 7/2010 |
| WO | WO-1996/025089 | 8/1996 |
| WO | WO-1996/035370 | 11/1996 |
| WO | WO-1997/015227 | 5/1997 |
| WO | WO-2000/049940 | 8/2000 |
| WO | WO-2000/059370 | 10/2000 |
| WO | WO-2000/074753 | 12/2000 |
| WO | WO-2001/052935 | 7/2001 |
| WO | WO-2001/054753 | 8/2001 |
| WO | WO-2002/016905 | 2/2002 |
| WO | WO-2003/076893 | 9/2003 |
| WO | WO-2003/082091 | 10/2003 |
| WO | WO-2004/060455 | 7/2004 |
| WO | WO-2005/065542 | 7/2005 |
| WO | WO-2006/024671 | 3/2006 |
| WO | WO-2006/081336 | 8/2006 |
| WO | WO-2006/085087 | 8/2006 |
| WO | WO-2006/110193 | 10/2006 |
| WO | WO-2007/097754 | 8/2007 |
| WO | WO-2008/001366 | 1/2008 |
| WO | WO-2008/086541 | 7/2008 |

OTHER PUBLICATIONS

Arnold, M. A., et al., "Selectivity Assessment of Noninvasive Glucose Measurements Based on Analysis of Multivariate Calibration Vectors", Journal of Diabetes Science and Technology, vol. 1, No. 4, 2007, pp. 454-462.

Bennion, N., et al., "Alternate Site Glucose Testing: A Crossover Design", Diabetes Technology & Therapeutics, vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Boyne, M. S., et al., "Timing of Changes in Interstitial and Venous Blood Glucose Measured With a Continuous Subcutaneous Glucose Sensor", Diabetes, vol. 52, Nov. 2003, pp. 2790-2794.

Bremer, T. M., et al., "Benchmark Data from the Literature for Evaluation of New Glucose Sensing Technologies", Diabetes Technology & Therapeutics, vol. 3, No. 3, 2001, pp. 409-418.

Brooks, S. L., et al., "Development of an On-Line Glucose Sensor for Fermentation Monitoring", Biosensors, vol. 3, 1987/88, pp. 45-56.

Cass, A. E., et al., "Ferrocene-Medicated Enzyme Electrode for Amperometric Determination of Glucose", Analytical Chemistry, vol. 56, No. 4, 1984, 667-671.

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.

Choleau, C., et al., "Calibration of a Subcutaneous Amperometric Glucose Sensor Implanted for 7 Days in Diabetic Patients Part 2. Superiority of the One-Point Calibration Method", Biosensors and Bioelectronics, vol. 17, No. 8, 2002, pp. 647-654.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Dassau, E., et al., "Detection of a Meal Using Continuous Glucose Monitoring", Emerging Treatments and Technologies, vol. 31, No. 2, Feb. 2008, pp. 295-300.

Diabetes Control and Complications Trial Research Group, "The Effect of Intensive Treatment of Diabetes on the Development and Progression of Long-Term Complications in Insulin-Dependent Diabetes Mellitus," New England J. Med. vol. 329, 1993, pp. 977-986.

Eren-Oruklu, M., et al., "Estimation of Future Glucose Concentrations with Subject-Specific Recursive Linear Models", Diabetes Technology & Therapeutics vol. 11(4), 2009, pp. 243-253.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Guerci, B., et al., "Clinical Performance of CGMS in Type 1 Diabetic Patients Treated by Continuous Subcutaneous Insulin Infusion Using Insulin Analogs", Diabetes Care, vol. 26, 2003, pp. 582-589.

Hovorka, R., et al., "Nonlinear Model Predictive Control of Glucose Concentration in Subjects with Type 1 Diabetes", Physiological Measurement, vol. 55, Jul. 2004, pp. 905-920.

Hyunjin, L., et al., "A Closed-Loop Artificial Pancreas Using Model Predictive Control and a Sliding Meal Size Estimator", Journal of Diabetes Science and Technology, vol. 3, Issue 5, Sep. 2009, pp. 1082-1090.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Kovatchev, B. P., et al., "Evaluating the Accuracy of Continuous Glucose-Monitoring Sensors", Diabetes Care, vol. 27, No. 8, 2004, pp. 1922-1928.

Kovatchev, B. P., et al., "Graphical and Numerical Evaluation of Continuous Glucose Sensing Time Lag", Diabetes Technology & Therapeutics, vol. 11, No. 3, 2009, pp. 139-143.

Kuure-Kinsey, M., et al., "A Dual-Rate Kalman Filter for Continuous Glucose Monitoring", Proceedings of the 28th IEEE, EMBS Annual International Conference, New York City, 2006, pp. 63-66.

Lodwig, V., et al., "Continuous Glucose Monitoring with Glucose Sensors: Calibration and Assessment Criteria", Diabetes Technology & Therapeutics, vol. 5, No. 4, 2003, pp. 573-587.

(56) References Cited

OTHER PUBLICATIONS

Lortz, J., et al., "What is Bluetooth? We Explain the Newest Short-Range Connectivity Technology", Smart Computing Learning Series, Wireless Computing, vol. 8, Issue 5, 2002, pp. 72-74.
Malin, S. F., et al., "Noninvasive Prediction of Glucose by Near-Infrared Diffuse Reflectance Spectoscopy", Clinical Chemistry, vol. 45, No. 9, 1999, pp. 1651-1658.
Mcgarraugh, G., et al., "Glucose Measurements Using Blood Extracted from the Forearm and the Finger", TheraSense, Inc., 2001, 16 Pages.
Mcgarraugh, G., et al., "Physiological Influences on Off-Finger Glucose Testing", Diabetes Technology & Therapeutics, vol. 3, No. 3, 2001, pp. 367-376.
Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.
Mougiakakou, et al., "A Real Time Simulation Model of Glucose-Insulin Metabolism for Type 1 Diabetes Patients", Proceedings of the 2005 IEEE, 2005, pp. 298-301.
Panteleon, A. E., et al., "The Role of the Independent Variable to Glucose Sensor Calibration", Diabetes Technology & Therapeutics, vol. 5, No. 3, 2003, pp. 401-410.
Parker, R., et al., "Robust H∞ Glucose Control in Diabetes Using a Physiological Model", AIChE Journal, vol. 46, No. 12, 2000, pp. 2537-2549.
Pickup, J., et al., "Implantable Glucose Sensors: Choosing the Appropriate Sensing Strategy", Biosensors, vol. 3, 1987/88, pp. 335-346.
Pickup, J., et al., "In Vivo Molecular Sensing in Diabetes Mellitus: An Implantable Glucose Sensor with Direct Electron Transfer", Diabetologia, vol. 32, 1989, pp. 213-217.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", The American Physiological Society, 1995, E155-E161.
Roe, J. N., et al., "Bloodless Glucose Measurements", Critical Review in Therapeutic Drug Carrier Systems, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.
Sakakida, M., et al., "Ferrocene-Mediated Needle-Type Glucose Sensor Covered with Newly Designed Biocompatible Membrane", Sensors and Actuators B, vol. 13-14, 1993, pp. 319-322.
Salehi, C., et al., "A Telemetry-Instrumentation System for Long-Term Implantable Glucose and Oxygen Sensors", Analytical Letters, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas With Needle-Type Glucose Sensor", The Lancet, 1982, pp. 1129-1131.
Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Steil, G. M., et al., "Determination of Plasma Glucose During Rapid Glucose Excursions with a Subcutaneous Glucose Sensor", Diabetes Technology & Therapeutics, vol. 5, No. 1, 2003, pp. 27-31.
Steil, G.M., et al., "Closed-Loop Insulin Delivery—the Path of Physiological Glucose Control", Advanced Drug Delivery Reviews, vol. 56, 2004, pp. 125-144.
Sternberg, R., et al., "Study and Development of Multilayer Needle-Type Enzyme-Based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A., et al., "Diabetes Mellitus: Biosensors for Research and Management", Biosensors, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.
Velho, G., et al., "Strategies for Calibrating a Subcutaneous Glucose Sensor", Biomedica Biochimica Acta, vol. 48, 1989, pp. 957-964.
Wilson, G. S., et al., "Progress Toward the Development of an Implantable Sensor for Glucose", Clinical Chemistry, vol. 38, No. 9, 1992, pp. 1613-1617.
PCT Application No. PCT/U2015/023380, International Search Report and Written Opinion of the International Searching Authority dated Jun. 29, 2015.
European Patent Application No. 15773809.7, Extended European Search Report dated Oct. 25, 2017.
EP, 22178180.0 Extended Search Report, dated Feb. 22, 2023.
EP, 20198318.6 Extended Search Report, dated Jul. 8, 2021.

\* cited by examiner

METHOD AND APPARATUS FOR DETERMINING MEAL START AND PEAK EVENTS IN ANALYTE MONITORING SYSTEMS

CROSS-REFERENCE TO RELATED APPLICATIONS

The present application is a continuation of U.S. patent application Ser. No. 15/300,711, filed Sep. 29, 2016, which is a national stage patent application under 35 U.S.C. § 371 claims priority to PCT Application Serial No. PCT/US2015/23380, filed Mar. 30, 2015, which claims priority to and the benefit of U.S. Provisional Patent Application Ser. No. 61/972,381, filed Mar. 30, 2014, all of which are incorporated by reference herein in their entireties for all purposes.

BACKGROUND

The detection of the concentration level of glucose or other analytes in certain individuals may be vitally important to their health. For example, the monitoring of glucose levels is particularly important to individuals with diabetes or pre-diabetes. People with diabetes may need to monitor their glucose levels to determine when medication (e.g., insulin) is needed to reduce their glucose levels or when additional glucose is needed.

Devices have been developed for automated in vivo monitoring of analyte time series characteristics, such as glucose levels, in bodily fluids such as in the blood stream or in interstitial fluid. Some of these analyte level measuring devices are configured so that at least a portion of a sensor of an on-body device is positioned below a skin surface of a user, e.g., in a blood vessel or in the subcutaneous tissue of a user. As used herein, the term analyte monitoring system is used to refer to any type of in vivo monitoring system that uses a sensor disposed with at least a subcutaneous portion to measure and store sensor data representative of analyte concentration levels automatically over time.

Existing approaches to determining pre-prandial and post-prandial meal responses are achieved in several ways. One way to determine the pre-prandial and post-prandial meal responses uses paired fingerstick blood glucose tests, where glucose measurements are taken at the start of the meal and at a certain relative duration since the meal start. In this approach, however, the variability of duration between start and peak of meals results in estimation errors of the meal response. Another approach to determine pre-prandial and post-prandial meal responses uses a collection of dense glucose measurements (e.g. once every 10 minutes) in conjunction with user entered meal markers. However, as most meal markers only indicate the start of the meal, the availability and accuracy of such markers are affected by the patient's schedule and other unforeseeable circumstances. Yet another approach to determining pre-prandial and post-prandial meal responses includes collection of dense glucose measurement and a pre-determined time of day window, where glucose values within a particular time of day window are assumed to represent pre-breakfast, post-breakfast, for example. However, in this approach, the reliability of the estimates will largely depend upon the consistency in the patient's meal timing routine.

SUMMARY

Accordingly, embodiments of the present disclosure provide systems, methods, and apparatus for estimating or detecting start of meal event and peak meal response based on real time or pseudo-retrospective, or retrospective analysis of data corresponding to monitored analyte levels, which can be used to modify insulin therapy regimen such as adjusting the basal delivery rate for pump users, and/or adjusting bolus dose levels.

Certain embodiments of the present disclosure include performing conditioning on a plurality of data points corresponding to monitored analyte level over a first time period, for each data point, determining a time derivative based on the conditioned plurality of data points, determining optima of acceleration based on the determined time derivatives, removing false carbohydrate intake start and peak carbohydrate intake response pairs having an amplitude below a predetermined level, removing carbohydrate intake start candidate from the most current carbohydrate intake peak response candidate, removing unpaired carbohydrate intake start candidates and signal artifact falsely identified as carbohydrate intake start and carbohydrate intake peak response pair, and refining the identified carbohydrate intake start and peak carbohydrate intake response pairs.

Certain embodiments of the present disclosure include a user interface component and one or more processors operatively coupled to the user interface component, the one or more processors configured to perform conditioning on a plurality of data points corresponding to monitored analyte level over a first time period, for each data point, to determine a time derivative based on the conditioned plurality of data points, to determine optima of acceleration based on the determined time derivatives, to remove false carbohydrate intake start and peak carbohydrate intake response pairs having an amplitude below a predetermined level, to remove carbohydrate intake start candidate from the most current carbohydrate intake peak response candidate, to remove unpaired carbohydrate intake start candidates and signal artifact falsely identified as carbohydrate intake start and carbohydrate intake peak response pair, and to remove the identified carbohydrate intake start and peak carbohydrate intake response pairs.

Numerous other aspects and embodiments are provided. Other features and aspects of the present disclosure will become more fully apparent from the following detailed description, the appended claims, and the accompanying drawings.

BRIEF DESCRIPTION OF THE FIGURES

The accompanying drawings, which are incorporated herein, form part of the specification. Together with this written description, the drawings further serve to explain the principles of, and to enable a person skilled in the relevant arts, to make and use the present disclosure.

DETAILED DESCRIPTION

Figure 1:
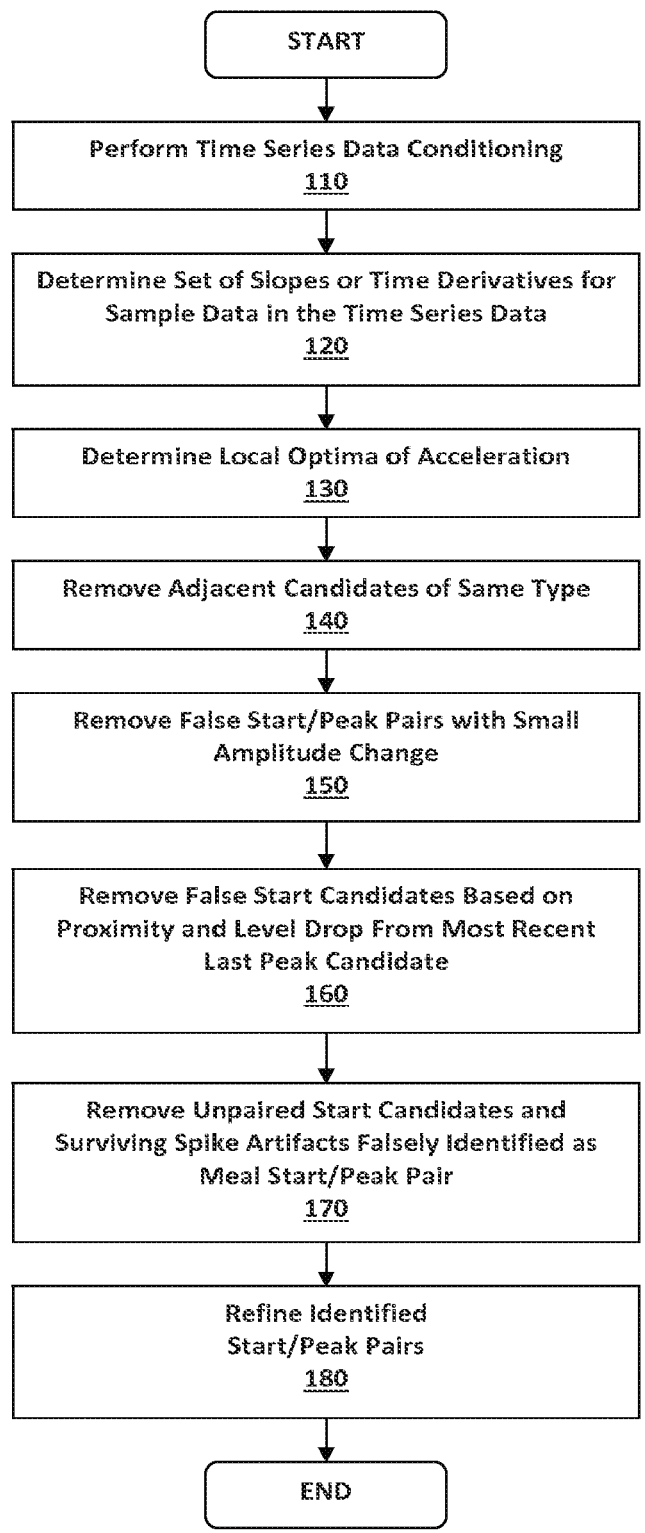
FIG. 1 illustrates a flowchart for meal start and peak detection routine in accordance with certain embodiments of the present disclosure.

Before the embodiments of the present disclosure are described, it is to be understood that this disclosure is not limited to the particular embodiments described, as such may, of course, vary. It is also to be understood that the terminology used herein is for the purpose of describing particular embodiments only, and is not intended to be limiting, since the scope of the embodiments of the disclosure will be limited only by the appended claims.

The present disclosure provides systems, methods, and apparatus to determine meal start and peak events based on analysis of information associated with monitored analyte concentration level. According to embodiments of the present disclosure, a dataset representative of a patient's monitored analyte concentration level (herein referred to as "sensor data") over time is received from an on-body device that includes sensor electronics operatively coupled to an analyte sensor that is in fluid contact with interstitial fluid. In some embodiments, the sensor data may represent a collection of data received from the on-body device at several different times during a wear period of the on-body device. In some other embodiments, the sensor data may represent data collected and stored over an entire wear period of the on-body device and only received from the on-body device at the end of the wear period or at the end of the useful life of the on-body device. In other words, the sensor data can be transmitted continuously, on a regular schedule, in multiple batches over time, in batches on demand, or in a single batch.

Embodiments of the present disclosure may be applied to any analyte concentration level determination system that may exhibit or at least be suspected of exhibiting, or that may be susceptible to noise in the sensor data. Embodiments of the disclosure are described primarily with respect to continuous glucose monitoring devices and systems but the present disclosure may be applied to other analytes and analyte characteristics, as well as data from measurement systems that transmit sensor data from a sensor unit to another unit such as a processing or display unit in response to a request from the other unit. For example, other analytes that may be monitored include, but are not limited to, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In the embodiments that monitor more than one analyte, the analytes may be monitored at the same or different times. The present disclosure also provides numerous additional embodiments.

Embodiments of the present disclosure may include a programmed computer system adapted to receive and store data from an analyte monitoring system. The computer system may include one or more processors for executing instructions or programs that implement the methods described herein. The computer system may include memory and persistent storage devices to store and manipulate the instructions and sensor data received from the analyte monitoring system. The computer system may also include communications facilities (e.g., wireless and/or wired) to enable transfer of the sensor data from the analyte monitoring system to the computer. The computer system may include a display and/or output devices for identifying dropouts in the sensor data to a user. The computer system may include input devices and various other components (e.g., power supply, operating system, clock, etc.) that are typically found in a conventional computer system. In some embodiments, the computer system may be integral to the analyte monitoring system. For example, the computer system may be embodied as a handheld or portable receiver unit within the analyte monitoring system.

Embodiments of the present disclosure perform analysis on analyte (e.g., glucose) data collected from analyte monitoring systems that includes a combination of asynchronous real-time and time spaced (e.g., 5 minutes-, 10 minutes-, 15 minutes-, 20 minutes-, 30 minutes-apart historical glucose data such as in flash glucose monitoring (FGM) systems, to be processed for analyte pattern and titration analysis. Embodiments also include analysis of mixed data collected from any of the following systems: discrete blood glucose monitoring (DGM) systems, continuous glucose monitoring (CGM) systems, in addition to flash glucose monitoring (FGM) systems. In this manner, embodiments of the present disclosure provide improved reliability of glucose pattern and titration analysis by distinguishing between true glucose trends and measurement errors, artifacts, and gaps caused by the measurement timing and/or process.

Prior approaches took pre-defined windows of time (e.g. entire 14 day sensor data collected, or 24 hours) to calculate glucose variability and median glucose. Such an approach analyzed each glucose reading independently, regardless of the relative timing and physiological feasibility of the relative magnitudes of glucose values. On the other hand, embodiments of the present disclosure perform physiological feasibility checks by comparing analyte level readings that are spaced close in time to obtain a more reliable estimate of glucose values.

Embodiments of the present disclosure includes first identifying and removing questionable data, where physiological limits are used to compare each measurement in the context of other nearby measurements, and thereafter, performing data conditioning and recovery including, for example, where surviving sampled data are conditioned, by signal processing, to minimize the amount of noise as much as possible, and the removed sampled data are supplemented by data based on other sampled data in close proximity to it in time. For example, performing data conditioning and recovery procedure includes data analysis routines described in pending U.S. patent application Ser. No. 14/210,312 entitled "Noise rejection Methods and Apparatus for Sparsely Sampled Analyte Sensor Data" filed on Mar. 13, 2014, the disclosure of which is incorporated herein by reference for all purposes.

Embodiments of the present disclosure include estimating the start time and peak instances of meal events based on sampled analyte data such as glucose measurement data, which can be used to improve the reliability of existing start-of-meal markers manually entered by the user.

In certain embodiments, the following assumptions are made when the algorithm performs data processing to determine the start and the peak of a meal event. For example, it is assumed that each meal event is far enough apart in time such that the initial change in glucose rise and the subsequent reversal is discernible from signal artifacts that may exist in the available sensor data measurements. Furthermore, the interaction between a meal and insulin is such that insulin cannot perfectly cancel the change in glucose due to the meal. This excludes clamps where both dextrose and insulin are intravenously administered at near constant infusion rates. Also, a meal may have insufficient insulin bolus, which would result in a higher post prandial glucose level than the pre-prandial glucose level, and may still continue to rise afterwards. In other words, the glucose response looks like the superposition of an increasing ramp and a textbook meal response (i.e. starting at a certain value, rising rapidly at the start of the meal, and decreasing at a slightly slower rate than the rate of increase). Accordingly, in certain embodiments, the glucose data are screened for local acceleration optima (ie. minima or maxima) as the initial candidate, and further refines the candidate start and peak instances by eliminating false candidates and adjusting the position of the final set of candidates.

Figure 6:
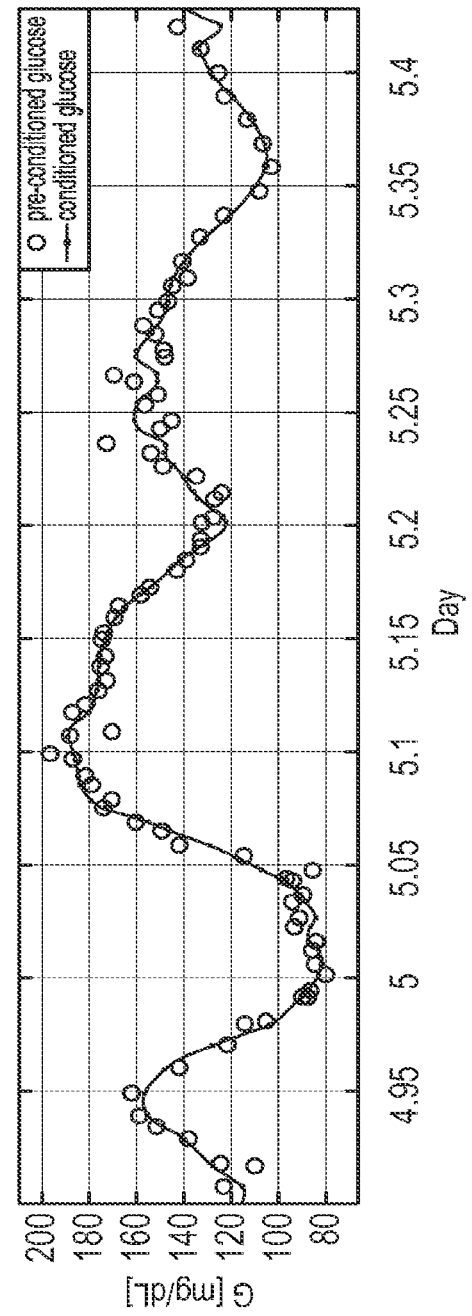
FIG. 6 illustrates data conditioning and/or data recovery for smooth output in conjunction with the routines above in certain embodiments of the present disclosure.

FIG. 1 illustrates a flowchart for meal start and peak detection routine in accordance with certain embodiments of the present disclosure. Referring to FIG. 1, sampled analyte (e.g. glucose) data from analyte monitoring systems or devices are collected or received and time series data conditioning is performed (110) that includes, for example, data conditioning to remove questionable readings from the sampled data and smoothing out the final result as described in detail below in conjunction with FIGS. 2-4. In certain embodiments, the data conditioning results in generating regularly spaced glucose values from irregularly sampled data. In certain embodiments, data conditioning includes determining whether sampled glucose data may be outliers when compared to sampled glucose data that are temporally in close proximity with each other. FIG. 6 illustrates data conditioning and/or data recovery for smooth output in conjunction with the routines above in certain embodiments of the present disclosure.

Referring to FIG. 1, after performing time series data conditioning (110), for each sampled sensor data, a set of slopes for the sampled analyte data are determined (120). That is, for each sampled data, a set of time derivatives in each time instance k of the glucose time series is determined (120). Separate sets of slopes or time derivatives are calculated to determine peak and meal start candidates. The selection of the time window duration where these sets of time derivatives are to be determined from, in the order of a few hours, are tuned to detect meal responses and ignore transients and other unrelated elements of glucose time series progression. The number of sampled data involved depends on the relative timestamps associated with when the sampled data was acquired.

More specifically, in certain embodiments, the set of slopes for determining a peak candidate, is a pair of slopes; one generated by computing rate of change in a forward window, and another generated by computing rate of change in a backward time window. Specifically, in certain embodiments, determining the forward and backward time window rates of change for the peak candidate includes using the sampled glucose data that are in the forward time window (i.e. from the present measurement at k to its near future time instance, such as 2~3 hours later) for the peak candidate, and then fit a straight line using Least-Squares error (LS) fit method. The slope is the forward rate of change for the peak candidate, v_peak_fwd(k). Further, determining the backward window rate includes using sampled glucose data that are in the backward window (i.e. from the present measurement at k to its near past time instance, such as 1~2 hours prior) for the peak candidate, and then fit a straight line using Least-Squares error (LS) fit method. The slope is the backward rate of change for the peak candidate, v_peak_bck(k).

In addition, the set of slopes for determining a meal start candidate is a pair of slopes; one generated by computing rate of change in a forward window, and another generated by computing rate of change in a backward time window. More specifically, in certain embodiments, determining forward and backward window rates of change for the meal start candidate includes using the sampled glucose data that are in the forward window (i.e. from the present measurement at k to its near future time instance, such as 1~1.5 hours later) for the meal start candidate, and then fit a straight line using Least-Squares error (LS) fit method. The slope is the forward rate of change for the meal start candidate, v_start_fwd(k). In certain embodiments, the forward window for peak and meal start candidates does not necessarily have the same width. Further, determining the backward window rate includes using sampled glucose data that are in the backward window (i.e. from the present measurement at k to its near past time instance, such as 2~3 hours prior) for the meal start candidate, and then fit a straight line using Least-Squares error (LS) fit method. The slope is the backward rate of change for the meal start candidate, v_start_bck(k). In certain embodiments, the backward window for peak and meal start candidates does not necessarily have the same width.

Referring to FIG. 1, the slope determination or determination of time derivatives for sampled data in the time series data (120) in certain embodiments includes determining the acceleration for the peak candidate, a_peak(k), where the acceleration for the peak candidate, a_peak(k), is defined as (v_peak_fwd(k)-v_peak_bck(k))/T_peak, where T_peak is a pre-determined sample period scaling factor for the peak candidate determination (for example, 1~3 hours).

Further, the slope determination or determination of time derivatives for sampled data in the time series data (120) further includes determining the acceleration for the start candidate, a_start(k), where acceleration for the start candidate, a_start(k) is defined as (v_start_fwd(k)-v_start_bck (k))/T_start, where T_start is a pre-determined sample period scaling factor for the meal start candidate determination (for example, 1~3 hours).

Figure 7:
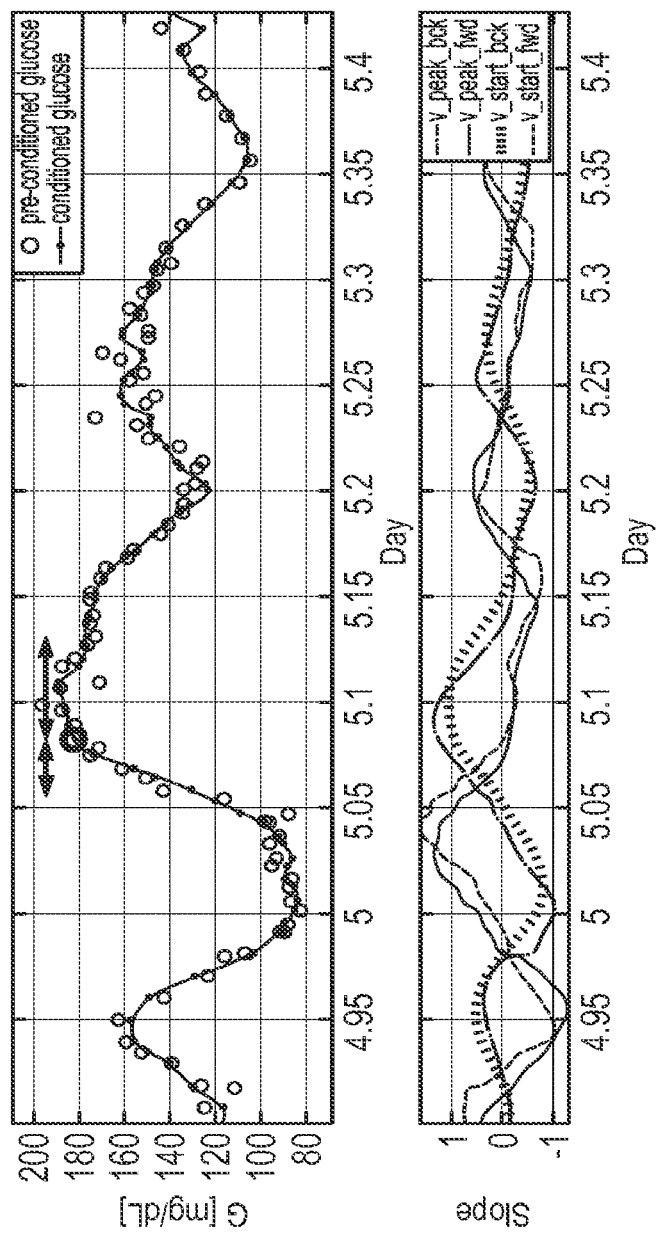
FIG. 7 illustrates determination of backward and forward slopes for peak and meal start candidates in conjunction with the routines above in certain embodiments of the present disclosure.

In this manner, in certain embodiments, the determination of time derivatives for sampled data in the time series data (120) includes slope or rate of change determination for each instance k of the sampled data, as shown for example, in FIG. 7. More specifically, FIG. 7 illustrates determination of backward and forward slopes for peak and meal start candidates in conjunction with the routines above in certain embodiments of the present disclosure. Referring to FIG. 7, circled sampled glucose data measurement instance and the nearby arrows illustrate the approximate size of the forward (to the right of the measurement instance) and backward (to the left of the measurement instance) time windows for the slope determinations.

Referring back to FIG. 1, after the determination of time derivatives for sampled data in the time series data (120), the local optima of acceleration is determined (130). More specifically, in certain embodiments, the local optima of acceleration are identified based upon signal analysis to identify extreme bend points. More specifically, in certain embodiments, at each time instance k, the determined acceleration for the peak candidate, a_peak, that falls within the forward window (incorporating data from present to 1~2 hrs later) for the peak candidate is determined, with the exception of the value at time instance k, a_peak(k). Further, at each time instance k, value a_peak that falls within the backward window (incorporating data from 1~2 hrs before to the present) for the peak candidate is determined, with the exception of the value at time instance k, a_peak(k). If the value a_peak(k) is less than or equal to the minimum a_peak values in the two aforementioned windows, the current time instance k is determined as a peak candidate during the determination of local optima of acceleration (130).

Figure 8:
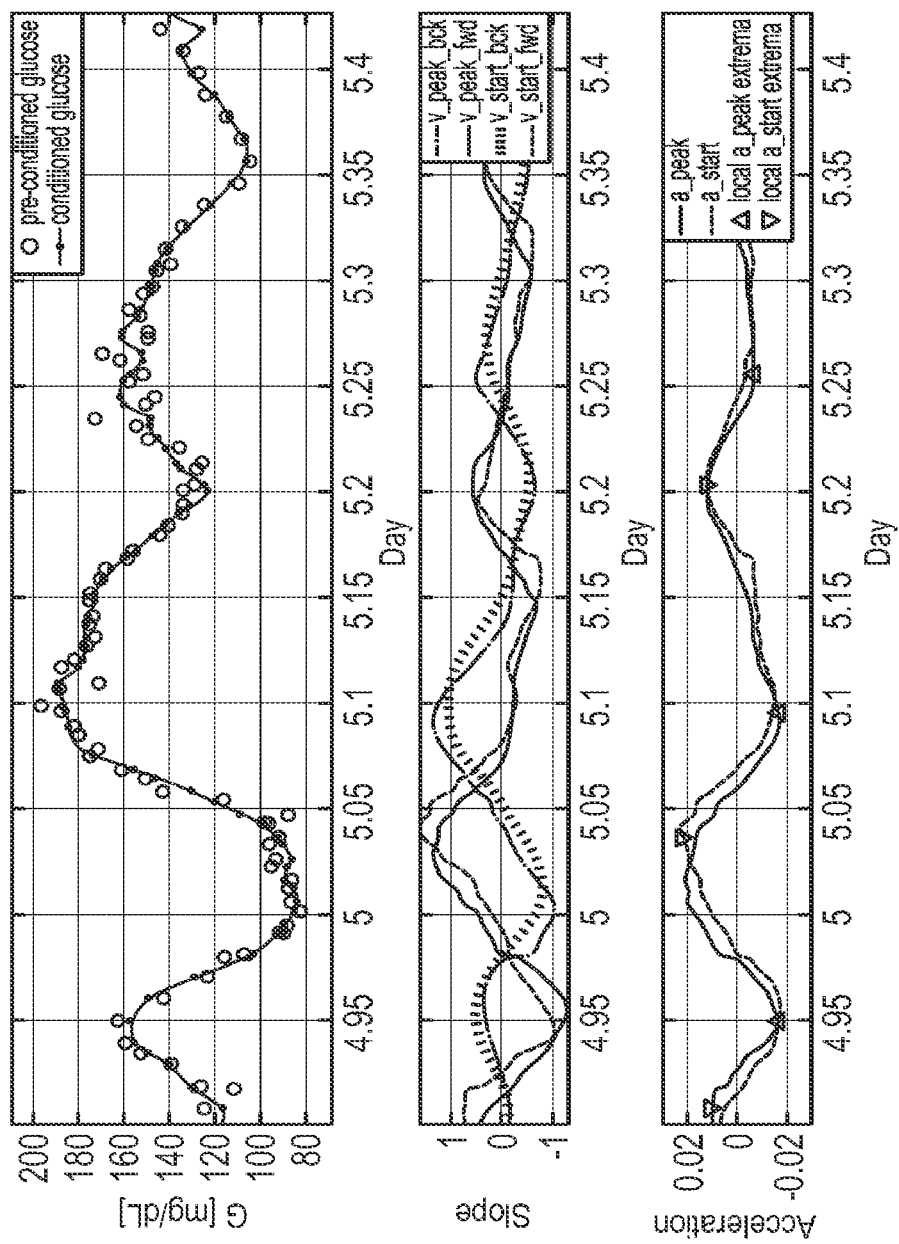
FIG. 8 illustrates determination of acceleration and the identification of local acceleration optima in conjunction with the routines above in certain embodiments of the present disclosure.

At each time instance k, the determined acceleration for the meal start candidate, a_start, that falls within the forward window (incorporating data from present to 1~2 hrs later) for the meal start candidate is determined, with the exception of the value at time instance k, a_start(k). At each time instance k, value a_start that falls within the backward window (incorporating data from 1~2 hrs before to the present) for the meal start candidate is determined, with the exception of the value at time instance k, a_start(k). If the value a_start(k) is greater than or equal to the maximum a_start values in the two aforementioned windows, then the current time instance k is determined as a meal start candidate during the determination of local optima of acceleration (130). In certain embodiments, if a time instance k has been previously identified as a peak candidate, and is also identified as a meal start candidate, the meal start candidate tag is moved to the next instance k+1. FIG. 8 illustrates determination of acceleration and the identification of local acceleration optima in conjunction with the routines above in certain embodiments of the present disclosure. More specifically, FIG. 8 illustrates the identification of the peak and meal start candidates described above and as marked by up and down triangles on the acceleration plot of FIG. 8.

More specifically, in certain embodiments, from all instances k of sampled glucose data in a time series, an initial subset of data is generated that includes all instances, m, identified or tagged as either a peak or meal start candidate from local optima of acceleration determination (130). For example, from each sampled glucose measurement instance k=1, 2, 3, . . . 10000, of 10000 measurement points, 5 candidates are identified from instances k=100, 150, 300, 400, and 700. The 5 candidate instances m=1, 2, 3, 4, 5, would be associated with the original instances as follows: the first candidate instance m=1 corresponds to the original instance at k=100, and the $2^{nd}$ candidate instance m=2 corresponds to the original instance at k=150, etc.

Referring back to FIG. 1, after the determination of local optima of acceleration (130), data analysis continues to identify and remove false meal start and peak candidates. In a first stage of analysis and removal, adjacent candidates of the same type are removed (140). That is, since a meal start event cannot be adjacent in time to another meal start event, and similarly, a peak meal response event cannot be adjacent in time to another peak meal response event, during the first stage of analysis and removal, adjacent candidates of the same type are identified and removed from the data set under consideration.

More specifically, from the initial subset of data including all instances, m, a first stage list of peak and meal start candidates identified as adjacent candidates of the same type is generated. From this first stage list, peak candidates are removed because the next instance of an adjacent peak candidate has a larger glucose value. That is, a peak candidate is removed during the first stage based on the following criteria: (1) the next instance m+1 in the subset is also a peak candidate; (2) the next instance m+1 in the initial subset has a larger glucose value than the current instance m; and (3) the rate from the forward peak calculation of the current instance m, v_peak_fwd(m), is more than a non-negative noise floor v_min_rise (e.g. 0.5 mg/dL/min). Calculated rates of change whose absolute numbers are close to zero tend to contain a lot of noise. Additionally, in certain embodiments, a peak candidate is also removed during the first stage if the prior instance of an adjacent peak candidate has a larger glucose value, i.e., based on the following criteria: (1) the previous instance m−1 in the initial subset is also a peak candidate; and (2) previous instance m−1 in the initial subset has a larger glucose value than the current instance m.

Furthermore, in certain embodiments, from the first stage list, meal start candidates are removed because the previous instance of an adjacent meal start candidate has a smaller glucose value. That is, a meal start candidate is removed during the first stage based on the following criteria: (1) the previous instance m−1 in the initial subset is also a meal start candidate; (2) the previous instance m−1 in the initial subset has a smaller glucose value than the current instance m; and (3) the value a_start(m−1) is smaller than a_start(m). In addition, in certain embodiments, a meal start candidate is also removed during the first stage if the next instance of an adjacent meal start candidate has an equal or smaller glucose value, i.e., based on the following criteria: (1) the next instance m+1 in the initial subset is also a meal start candidate; and (2) the next instance m+1 has a glucose value that is either equal to or less than the glucose value than the current instance m.

Figure 9:
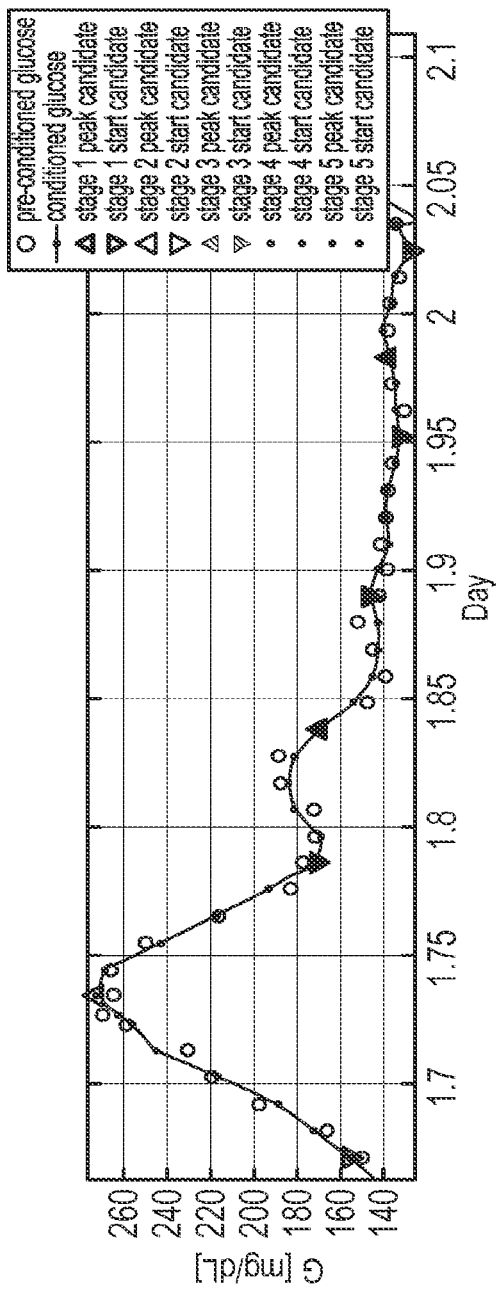
FIG. 9 illustrates an example of removal of adjacent candidates of the same type in conjunction with the routines above in certain embodiments of the present disclosure.

In this manner, in certain embodiments, adjacent meal start candidate or peak candidates of the same type are identified and removed from the data set under consideration. FIG. 9 illustrates an example of removal of adjacent candidates of the same type in conjunction with the routines above in certain embodiments of the present disclosure. More specifically, FIG. 9 is an example illustration of a meal start candidate at around 1.9 days that was identified during the local optima of acceleration determination (130), but was removed during the first stage of analysis and removal based on analysis determining the meal start candidate as adjacent candidate of the same type (140).

Referring again to FIG. 1, after removing adjacent candidates of the same type (140), the routine continues with a second stage of analysis and removal to identify and remove false meal start/peak pairs with small amplitude change (150). More specifically, in certain embodiments, an analysis is performed on the subset of remaining instances of peak candidates and meal start candidates following the first stage of removal based on adjacent candidates of the same type, i.e., a first stage subset. During the second stage, every peak candidate in the first stage subset is analyzed to determine whether the change in glucose value from the previous instance m−1, which would be a meal start candidate, to the current peak candidate m is sufficiently large. In other words, the current peak candidate m is removed from the first stage subset of tagged start or peak candidates when the following criteria are met: (1) previous instance m−1 in the first stage subset (after removal of adjacent candidates of the same type) is tagged as a meal start candidate; (2) the current instance m in the first stage subset is tagged as a peak candidate; and (3) the difference between the amplitude of the current instance m and the previous instance m−1 is less than or equal to g_min_amplitude, i.e. $g(m)-g(m-1) <= g\_min\_amplitude$, wherein g is the instance amplitude or level of glucose. Moreover, in certain embodiments, when a peak candidate is removed under these conditions, the corresponding meal start candidate, that is the previous instance m−1, is also removed.

By way of an example, FIG. 9 illustrates examples of removal of false meal start and peak candidate pairs with a small amplitude change in conjunction with the routines above in certain embodiments of the present disclosure. More specifically, FIG. 9 illustrates 2 pairs (around 1.8 days and 1.95 days) that were removed based on the analysis described herein to remove false meal start/peak pairs with small amplitude change.

Referring still to FIG. 1, after identifying and removing false meal start/peak pairs with small amplitude change (150), the routine continues with a third stage of analysis and removal to identify and remove false meal start candidates based on proximity and level drop from the most recent last peak candidate (160). That is, in certain embodiments, meal start candidates that are too close in time to a prior peak candidate and whose glucose value is not significantly lower than the glucose value of its prior peak candidate, are removed from the subset of remaining instances of peak candidates and meal start candidates following the second stage of removal, i.e., a second stage subset.

Figure 10:
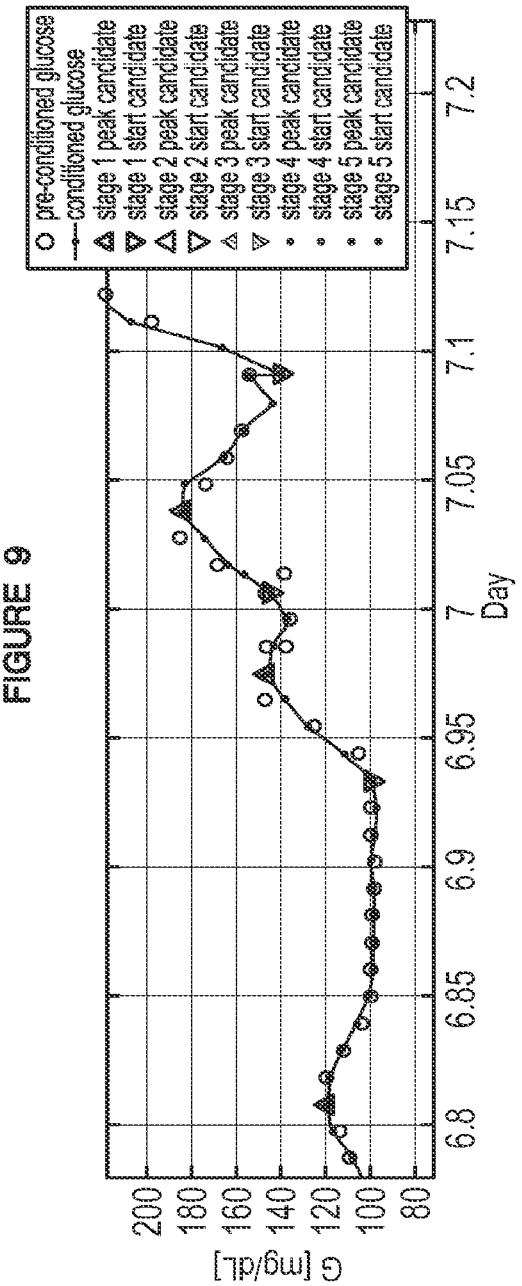
FIG. 10 illustrates examples of removal of false meal start and peak pairs with a small amplitude in conjunction with the routines above in certain embodiments of the present disclosure.

More specifically, in certain embodiments, during the third stage, it is determined whether the position of each meal start candidate with respect to a previous peak candidate is reasonable. That is, a meal start candidate at instance m is removed when the following criteria are met: (1) the previous instance m−1 in the second stage subset (after removal of start/peak pair with small amplitude change) is tagged as a peak candidate (e.g. see up triangle at around 6.975 days in FIG. 10); (2) the current instance m in the second stage subset is identified or tagged as a meal start candidate (e.g. see down triangle at around 7 days in FIG. 10); (3) the next instance m+1 in the second stage subset is identified or tagged as a peak candidate (e.g. see up triangle at around 7.04 days in FIG. 10); (4) the average value of v_start_bck(m) (see down triangle at around 7 days of FIG. 10) and v_peak_fwd(m−1) (see up triangle at around 6.975 days of FIG. 10) is greater than a maximum post-prandial recovery descent rate, v_max_descent (e.g. ¼ mg/dL/min); and (5) the difference between the glucose value of the current instance m and the previous instance m−1, $g(m)-g(m-1)$, is less than or equal to a minimum required drop from a previous peak, g_min_drop (e.g. 5~10 mg/dL). Moreover, when these criteria are met and a meal start candidate is removed, the peak candidate at the previous instance m−1, is also removed. FIG. 10 illustrates a meal start candidate at around 7 days that was removed, along with the prior peak candidate, due to proximity and level drop.

Referring again to FIG. 1, after removing meal start candidates based on proximity and level drop from the most recent last peak candidate (160), the routine continues, in certain embodiments, with a fourth stage of analysis and removal to identify and remove unpaired meal start candidates and surviving spike artifacts falsely identified as meal start/peak pairs (170). Surviving spike artifacts might happen if Time Series Data Conditioning (110) does not completely remove all artifacts. More specifically, in certain embodiments, surviving spike artifacts falsely identified as meal start/peak pairs, are removed from the subset of remaining instances of peak candidates and meal start candidates following the third stage of removal, i.e., a third stage subset. For each instance m in the third stage subset that is a start candidate, those whose next instance m+1 is not a peak candidate is removed. That is, a current meal start candidate at instance m is removed from the third stage subset if all of the following applies: (1) the current instance m is tagged as a meal start candidate; (2) the next instance m+1 is tagged as a peak candidate; and (3) the aggregate glucose rate of change, as calculated from $g(m+1)-g(m)$, divided by the time interval between the two instances m+1 and m, is larger than a maximum allowable initial post-prandial rate of change, v_max_initialSpike (e.g. 6 mg/dL/min, which is a rate of change that is likely not sustainable between two candidate points).

Figure 11:
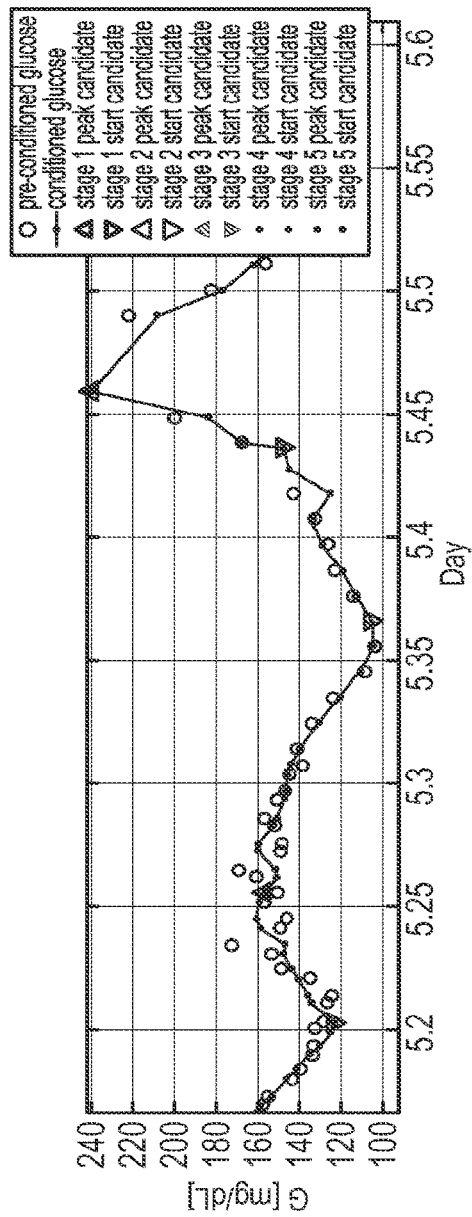
FIG. 11 illustrates removal of unpaired meal start candidates and surviving spike artifacts falsely identified as a meal start/peak pair in conjunction with the routines above in certain embodiments of the present disclosure.

Referring to the Figures, FIG. 11 illustrates removal of unpaired meal start candidates and surviving spike artifacts falsely identified as a meal start/peak pair in conjunction with the routines above in certain embodiments of the present disclosure. An example of a start candidate to be removed by this criteria is shown in FIG. 11, at around 5.35 days, where the next instance at around 5.44 days is also a start candidate.

In certain embodiments, because of the asymmetrical forward and backward time windows used to determine the pair v_start_fwd and v_start_bck, as well as the pair v_peak_fwd and v_peak_bck, and since a post-prandial meal response may be followed by a subsequent post-prandial meal response without sufficient time for the original post-prandial meal response to revert to the baseline or fasting glucose levels, the identification of meal start and peak candidate may be visibly biased slightly before or after the likely instance. Accordingly, in certain embodiments, these likely instances are analyzed and adjusted as discussed below.

More specifically, after the four stages of analysis and removal discussed above are complete, the remaining identified meal start and peak candidates are refined (180) in certain embodiments. That is, for each sampled glucose data time instance k, a simple forward and backward slope is determined. For example, all sampled glucose data measurement instances k are evaluated to refine the meal start and peak candidates remaining after the four stages of analysis and removal, identified in the subset of instances m. In certain embodiments, the time window sizes used in determining v_peak_fwd, v_peak_bck, v_start_fwd, v_start_bck, may be larger and asymmetric compared to the determinations steps that follow determining v_peak_fwd, v_peak_bck, v_start_fwd, v_start_bck. In this manner, false candidates due to signal artifacts are rejected earlier on in the routine as described in conjunction with FIG. 1, and by the start of the routine to refine the identified meal start and peak instances (180), the candidates are sufficiently localized to the true meal start and peak. Further, the smaller time windows provide a better precision in the determination.

In particular, for each sampled glucose data at instance k, g(k), an available sample that is as close to 30 minutes prior to k as possible, g_prev(k) is identified. Also, for each sampled glucose data at instance k, g(k), an available sample that is as close to 30 minutes after k as possible, g_after(k) is identified. Then, forward and backward slopes, v_fwd(k) and v_bck(k). v_fwd(k) are determined by taking the difference g_after(k)−g(k), and dividing it by their time interval (around 30 minutes). Also, backward slope v_bck(k) is calculated by taking the difference g(k)−g_prev(k), and dividing it by their time interval. The difference in slope, dv(k), is determined by taking the difference v_fwd(k)−v_bck(k).

For every instance k where a meal start or peak has been identified during removal of start candidates based on proximity and level drop analysis from most recent last peak candidate (160), the time instances in pairs of meal start and peak are identified.

For each identified meal start/peak pair a glucose time series, g_array_start, up to 90 minutes prior to the identified start candidate, and up to 60 minutes after the identified start candidate is defined. The defined glucose time series, g_array_start includes the meal start candidate that survived the data processing (110 to 170) in the routine described above in conjunction with FIG. 1. Also, a glucose time series, g_array_peak, up to 60 minutes prior to the identified peak candidate, and up to 180 minutes after the identified peak candidate is defined. The glucose time series, g_array_peak includes the peak candidate that survived the data processing (110 to 170) in the routine described above in conjunction with FIG. 1. Then, g_array_peak from any sampled glucose data are trimmed whose timestamp overlaps the start time of the next pair in the routine where the unpaired start candidates and surviving spike artifacts falsely identified as meal start/peak pair are removed (170). For each value in g_array_start and g_array_peak, the corresponding difference in slope values, dv are determined from the same instances. Arrays of these values, dv_array_start and dv_array_peak are defined.

Thereafter, in certain embodiments, a subset of time instances are determined such that (1) measured glucose value at these instances are greater than or equal to the $75^{th}$ percentile of g_array_peak, and (2) dv value at these instances are less than or equal to the $25^{th}$ percentile of dv_array_peak. If such a subset contains data, then the highest glucose value in this subset, g_max, and its corresponding instance, is stored. Furthermore, the routine determines a subset of time instances such that (1) measured glucose value at these instances are less than or equal to the $25^{th}$ percentile of g_array_start, and (2) dv value at these instances are greater than or equal to the $75^{th}$ percentile of dv_array_start. If such a subset contains data, then the lowest glucose value in this subset, g_min, and its corresponding instance, is stored. Then the peak and start candidate for this pair with the highest glucose value in the subset, g_max and the lowest glucose value in the subset, g_min, are updated based on the following criteria: (1) the lowest glucose value in the subset, g_min, and the highest glucose value in the subset, g_max, exist and are finite; (2) the instance of lowest glucose value in the subset, g_min, occurs prior to the instance of the highest glucose value in the subset, g_max; and (3) the lowest glucose value in the subset, g_min, is less than the highest glucose value in the subset, g_max.

Figure 12:
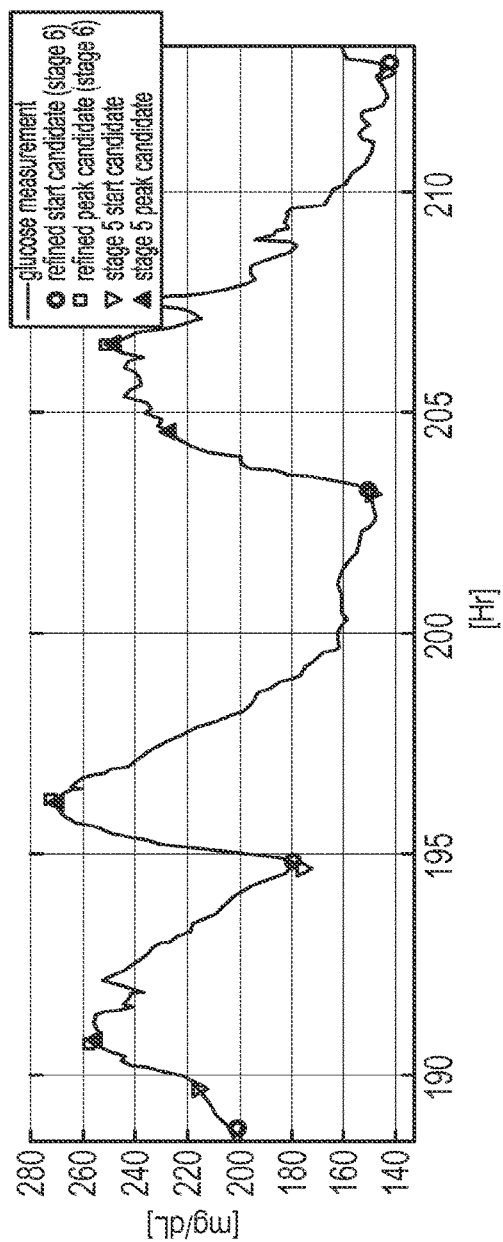
FIG. 12 illustrates refinement of identified meal start and peak instances in conjunction with the routines above in certain embodiments of the present disclosure.

FIG. 12 illustrates refinement of identified meal start and peak instances in conjunction with the routines above in certain embodiments of the present disclosure. More specifically, FIG. 12 provides an example illustration of the effect of the routine to refine the identified start/peak pairs (180) of FIG. 1 when glucose measurement is sampled at a relatively fast sample period of once every minute. For sparser sample periods (such as illustrated in FIG. 11), the number of sampled glucose data that can be a viable peak or meal start candidates are much smaller than faster sample periods. As a result, the refinement of identified meal start/peak pairs (180) is more useful in certain embodiments, around time periods with a lot of measurements than periods with sparse measurements.

Figure 13:
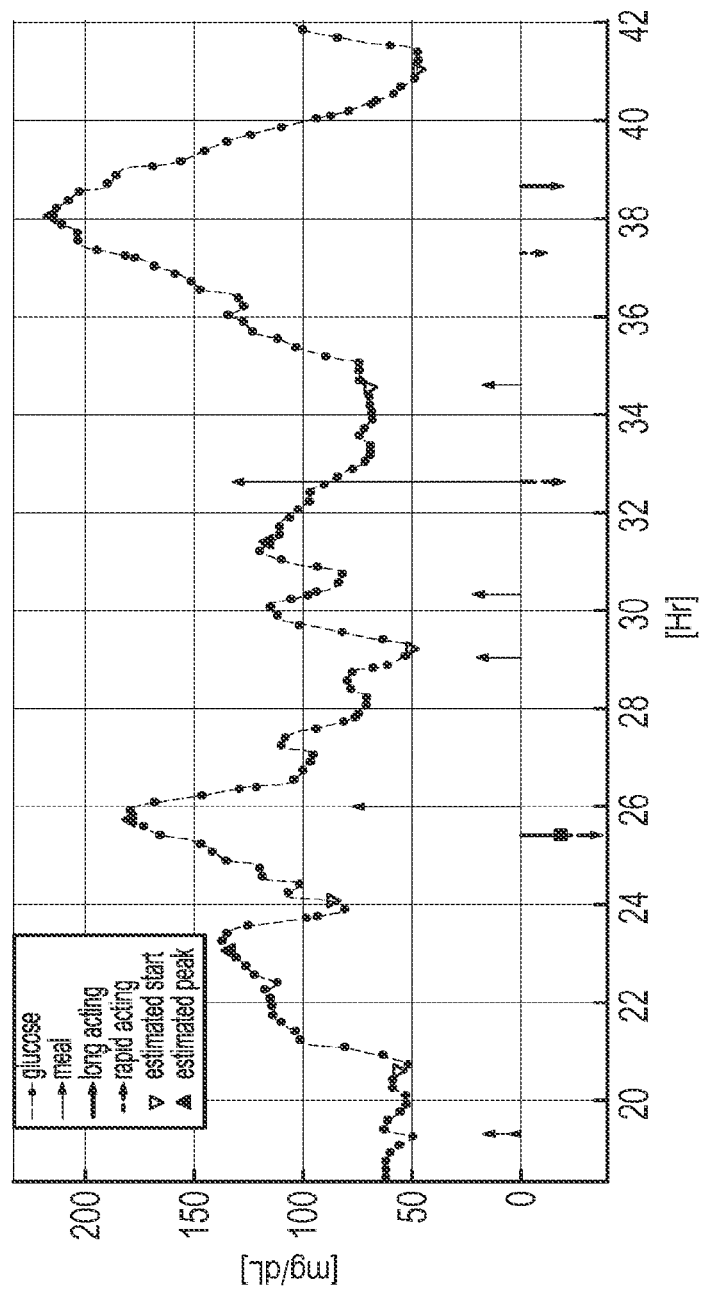
FIG. 13 illustrates an example of comparison of estimated meal start determination in conjunction with the routines described herein against manually marked meal start events.

FIG. 13 illustrates an example of comparison of estimated meal start determination in conjunction with the routines described herein against manually marked meal start events. Referring to FIG. 13, there is shown sampled glucose data from a patient, along with patient-recorded meal marker, long acting insulin, and rapid acting insulin. The estimated meal start and peak as described in conjunction with FIG. 1 above is also shown. The plot in FIG. 13 covers approximately one day, starting from a fasting period (up to around 21 hours since glucose sensor start (to acquire sampled glucose data)), followed by a series of meals, and a potentially unrecorded rescue carbohydrate at around hour 41. There are 7 meal markers recorded, two of them within a few minutes at around hour 19. It can be seen from FIG. 13 that the first two meal markers appear to correspond to the increase estimated at around hour 21. The third meal marker may be a late entry from the lunch at hour 24, and the subsequent two entries may be snacks. The two snacks were assumed as a single meal by the estimation routine in accordance with the embodiments of the present disclosure, due to an assumption about minimum duration of meals reflected in the duration of the forward and backward windows of the peak and start candidates during the local optima of acceleration determination. The last two may correspond to the bulk of dinner and a desert, although the glucose response seems to be delayed by about 3 hours.

Figure 2:
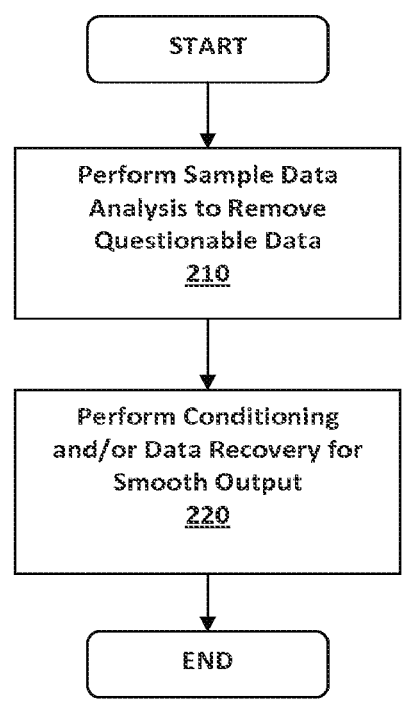
FIG. 2 illustrates a flowchart for performing time series sampled analyte data conditioning of the meal start and peak detection routine of FIG. 1 in accordance with certain embodiments of the present disclosure.

Referring back to the Figures, FIG. 2 illustrates a flowchart for performing time series sampled analyte data conditioning of the meal start and peak detection routine of FIG. 1 in accordance with certain embodiments of the present disclosure. Referring to FIGS. 1 and 2, performing time series sampled analyte data conditioning of the meal start and peak detection (110) in certain embodiments includes performing sampled data analysis to remove questionable data, where physiological limits are used to compare each sampled glucose data in the context of other temporally closely located sampled glucose data (210). Thereafter, data conditioning and/or recovery is performed to smooth the data output (220), where surviving sampled data are conditioned to minimize noise, and removed measurements are supplemented by sampled data based on other temporally closely located sampled data.

Figure 3:
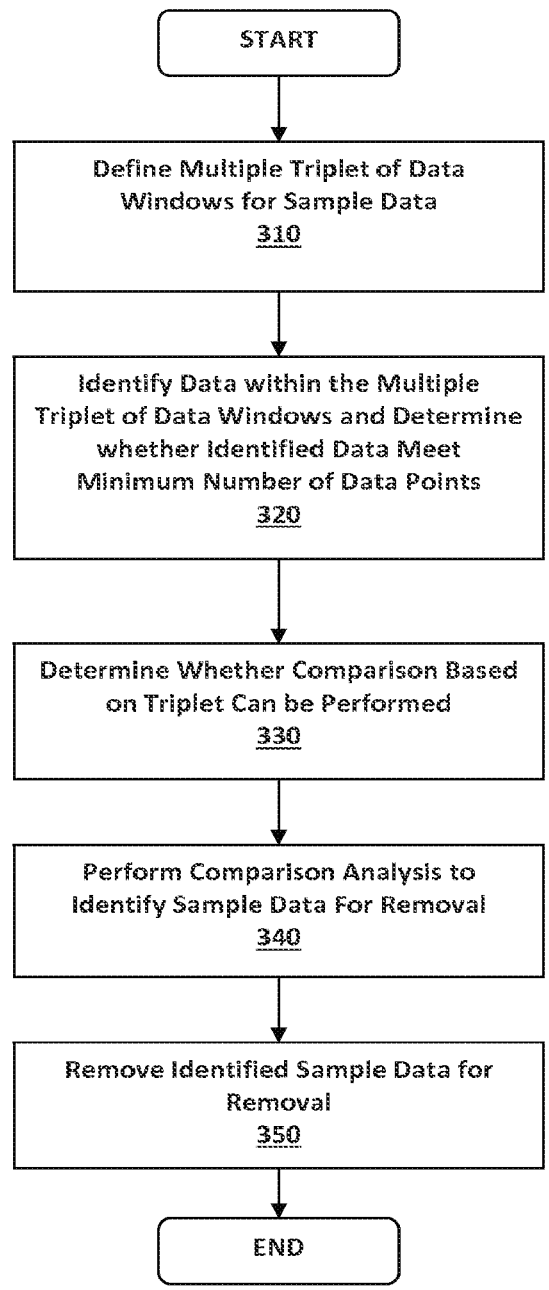
FIG. 3 illustrates a flowchart for sampled data analysis to remove questionable data of FIG. 2 in accordance with certain embodiments of the present disclosure.

FIG. 3 illustrates a flowchart for sampled data analysis to remove questionable data of FIG. 2 in accordance with certain embodiments of the present disclosure. Referring to FIG. 3, in certain embodiments, removal of questionable sampled glucose data includes data processing and analysis as described below. More specifically, for each sampled data instance, more than one triplet of time windows is defined to address data stream with a range of sample time intervals.

That is, a first triplet of left, center, and right time windows ScreenLeft1, ScreenCenter1, and ScreenRight1, respectively, are defined where (1) the left time window only looks at available measurements prior to the current instance (e.g. from 30 minutes ago to 3 minutes ago); (2) the right time window only looks at available measurements after the current instance (e.g. from 3 minutes to 30 minutes after the current instance); (3) the center time window only looks at available measurements slightly before the current instance and slightly after the current instance (e.g. within ±3 minutes of the current instance); and (4) each time window requires a minimum number of available points (e.g. 1 for the center time window, 2 for the left time window, and 2 for the right time window).

Furthermore, a second triplet of left, center, and right time windows ScreenLeft2, ScreenCenter2, and ScreenRight2, respectively are defined, where (1) left time window is narrower than that of ScreenLeft1 (e.g. from 15 minutes ago to 3 minutes ago), but requires a larger number of minimum available points (e.g. 6 points); (2) right time window is narrower than that of ScreenRight1 (e.g. from 3 minutes to 15 minutes after the current instance), but requires a larger number of minimum available points (e.g. 6 points); and (3) center time window requires a larger number of minimum available points (e.g. 4 points). Also, a maximum allowable range ScreenMaxRange and maximum allowable relative range ScreenMaxRelativeRange are defined to be used to compare multiple estimates based on the different time windows.

Referring back to FIG. 3, after defining multiple triplets of data windows for the sampled data (310), data within the multiple triplets of data windows are identified and it is determined whether the identified data meet the minimum number of data points (320). More specifically, for each sampled glucose data instance, measurements that fall within the multiple triplets of windows as set forth above are identified, and it is determined whether or not the number of available points in each time window meets the respective minimum number of points. Then, it is determined whether comparison based on each triplet can be performed (330) based on the following criteria: (1) comparison within the first triplet can be performed when there is sufficient number of measurements in ScreenCenter1, and either there is sufficient number of sampled data in ScreenLeft1 or ScreenRight1; and (2) comparison within the second triplet can be performed when there is sufficient number of measurements in ScreenCenter2, and either there is sufficient number of measurements in ScreenLeft2 or ScreenRight2.

Furthermore, for each sampled glucose data instance, if comparison within the first triplet can be performed the following routines are performed (340). More specifically, yCenter1, an estimate of current measurement instance based on ScreenCenter1, is determined by taking the average of available points in ScreenCenter1, yRight1, an estimate of current measurement instance based on ScreenRight1, is determined by performing a least-square error fit of a straight line using available points in ScreenRight1, evaluated at the instance of the current sampled data. The estimate of current measurement instance based on ScreenRight1, yRight1, is not determined if the number of points in ScreenRight1 is insufficient. Also, yLeft1, an estimate of current measurement instance based on ScreenLeft1, is determined by performing a least-square error fit of a straight line using available points in ScreenLeft1, evaluated at the instance of the current measurement. The estimate of current measurement instance, yLeft1, is not determined if the number of points in ScreenLeft1 is insufficient.

If comparison within the second triplet can be performed, yCenter2, an estimate of current measurement instance based on ScreenCenter2, is determined by performing a least-square error fit of a straight line using available points in ScreenCenter2, evaluated at the instance of the current measurement. The estimate of current measurement instance based on ScreenCenter2, yCenter2 is not determined if the number of points in ScreenCenter2 is insufficient. Also, yRight2, an estimate of current measurement instance based on ScreenRight2, is determined by performing a least-square error fit of a straight line using available points in ScreenRight2, evaluated at the instance of the current measurement. The estimate of current measurement instance based on ScreenRight2, yRight2 is not determined if the number of points in ScreenRight2 is insufficient. Additionally, yLeft2, an estimate of current measurement instance based on ScreenLeft2, is determined by performing a least-square error fit of a straight line using available points in ScreenLeft2, evaluated at the instance of the current measurement. The estimate of current measurement instance based on ScreenLeft2, yLeft2 is not determined if the number of points in ScreenLeft2 is insufficient. Then, estimates of the current measurement instance based on the first triplet, yCenter1, yRight1, and yLeft1, are updated by estimates based on the second triplet (e.g. assign the value of yCenter2 to yCenter1, assign the value of yRight2 to yRight1, and assign yLeft2 to yLeft1), if the determination is available.

In addition, for each sampled data instance, if comparison within the first triplet can be performed, available yCenter1, yLeft1, and yRight1 measurements are collected, and the following values are determined: (1) yAvg, the average of the available values, (2) yMin, the smallest of the available values, (3) yMax, the largest of the available values, (4) yRange, the absolute value of the difference between yMin and yMax, and (5) yRelativeRange, the value of yRange divided by yAvg. Then, the values yRelativeRange and yRange are compared against the thresholds ScreenMaxRelativeRange and ScreenMaxRange, respectively. If either one exceeds the threshold, the current sampled glucose data instance is identified for removal. In certain embodiments, identifying for removal of any sampled glucose data instance is not performed until all sampled glucose data instances have been evaluated.

On the other hand, for each sampled glucose data instance, if the comparison within the first triplet cannot be performed (340), the sampled glucose data instance is not identified for removal. Thereafter, sampled glucose data instances identified for removal are removed from the data set under analysis (350).

Figure 4:
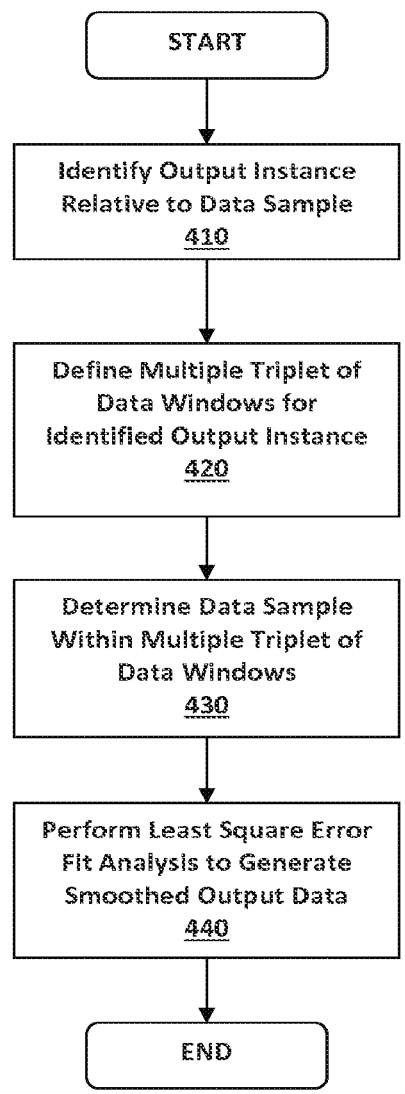
FIG. 4 illustrates a flowchart for data conditioning and/or data recovery for smooth output of FIG. 2 in accordance with certain embodiments of the present disclosure.

FIG. 4 illustrates a flowchart for data conditioning and/or data recovery for smooth output of FIG. 2 in accordance with certain embodiments of the present disclosure. Referring to FIGS. 2 and 4, in certain embodiments, data conditioning and/or recovery performed to smooth the data output (220) (FIG. 2) includes identifying output instance relative to data sample (410). That is, instances where output is desired is defined by, for example, (1) defining output instances as instances where the original sampled glucose data are found in which case, the output instances will take on the same timestamps as the original data, (2) defining output instances as instances where the original sampled glucose data are found, but were not marked for removal at step 210 (FIG. 2), or (3) defining output instances by a new arbitrary, but regular, sample interval (e.g. once every 8 minutes, or once every 30 minutes).

Referring back to FIG. 4, after identifying output instance relative to data sample (410), multiple triplet of data time windows for identified output instance is defined (420). More particularly, in certain embodiments, for each identified output instance, more than one triplet of time windows are defined to process data streams with a range of data sample time intervals. Specifically, in certain embodiments, a first triplet of left, center, and right windows SmoothLeft1, SmoothCenter1, and SmoothRight1, respectively, are defined where (1) left window, SmoothLeft1 only looks at available measurements prior to the current instance (e.g. from 50 minutes ago to 5 minutes ago); (2) right window, SmoothRight1 only looks at available measurements after the current instance (e.g. from 5 minutes to 50 minutes after the current instance); and (3) center window, SmoothCenter1 only looks at available measurements before the current instance and after the current instance (e.g. within ±32 minutes of the current instance). In certain embodiments, each window requires a minimum number of available points (e.g. 2 for the center window, 3 for the left window, and 3 for the right window).

Furthermore, in certain embodiments, for each identified output instance, more than one triplet of time windows are defined to process data streams with a range of data sample time intervals by defining a second triplet of left, center, and right windows SmoothLeft2, SmoothCenter2, and SmoothRight2, where (1) left window is narrower than that of SmoothLeft1 (e.g. from 20 minutes ago to 5 minutes ago), but requires a larger number of minimum available points (e.g. 9 points); (2) right window is narrower than that of SmoothRight1 (e.g. from 5 minutes to 20 minutes after the current instance), but requires a larger number of minimum available points (e.g. 9 points), and (3) center window is narrower than that of SmoothCenter1 (e.g. from 7 minutes prior to 7 minutes after the current instance), but requires a larger number of minimum available points (e.g. 9 points).

Referring again to FIG. 4, after defining multiple triplet of data time windows for identified output instance (420), for each output instance, sampled glucose data that fall within the defined multiple triplets of time windows are identified (430). It is also determined whether the number of available sampled glucose data points in each time window meets the respective minimum number of points.

Thereafter, Least Square error fit analysis is performed to generate smoothed output data (440). For example, in certain embodiments, ySmoothCenter1, an estimate of current output instance based on SmoothCenter1, is determined by performing a least-square error fit of a straight line using available points in SmoothCenter1, evaluated at the current output instance. The estimate of current output instance based on SmoothCenter1, ySmoothCenter1 is not determined if the number of points in this window is insufficient. Also, ySmoothRight1, an estimate of current output instance based on SmoothRight1, is determined by performing a least-square error fit of a straight line using available points in SmoothRight1, evaluated at the current output instance. The estimate of current output instance based on SmoothRight1, ySmoothRight1 is not determined if the number of points in this window is insufficient. In addition, ySmoothLeft1, an estimate of current output instance based on SmoothLeft1, is determined by performing a least-square error fit of a straight line using available points in SmoothLeft1, evaluated at the current output instance. The estimate of current output instance based on SmoothLeft1, ySmoothLeft1 is not determined if the number of points in this window is insufficient. Moreover, ySmoothCenter2, an estimate of current output instance based on SmoothCenter2, is determined by performing a least-square error fit of a straight line using available points in SmoothCenter2, evaluated at the current output instance. Similarly, the estimate of current output instance based on SmoothCenter2, ySmoothCenter2 is not determined if the number of points in this window is insufficient. Otherwise, ySmoothCenter1 is updated by assigning the value of ySmoothCenter2 to ySmoothCenter1. Further, ySmoothRight2, an estimate of current output instance based on SmoothRight1, is determined by performing a least-square error fit of a straight line using available points in SmoothRight2, evaluated at the current output instance. Again, the estimate of current output instance based on SmoothRight1, ySmoothRight2 is not determined if the number of points in this window is insufficient. Otherwise, ySmoothRight1 is updated by assigning the value of ySmoothRight2 to ySmoothRight1. Still further, ySmoothLeft2, an estimate of current output instance based on SmoothLeft2, is determined by performing a least-square error fit of a straight line using available points in SmoothLeft2, evaluated at the current output instance. The estimate of current output instance based on SmoothLeft2, ySmoothLeft2 is not determined if the number of points in this window is insufficient. Otherwise, ySmoothLeft1 is updated by assigning the value of ySmoothLeft2 to ySmoothLeft1.

Thereafter, ySmoothAvgSide, the average of available ySmoothRight1 and ySmoothLeft1 is determined. If both ySmoothCenter1 and ySmoothAvgSide can be determined, ySmooth, the smoothed, final output for this output instance is determined, by assigning ySmooth as the average of ySmoothCenter1 and ySmoothAvgSide.

In the manner described above, in certain embodiments, the meal start and peak estimation routine includes performing sample data analysis to remove questionable data (210) and then performing data conditioning and/or data recovery for smooth output (220) to perform time series data conditioning (110) before the time derivatives for sample data in the time series data are determined (120).

Figure 5:
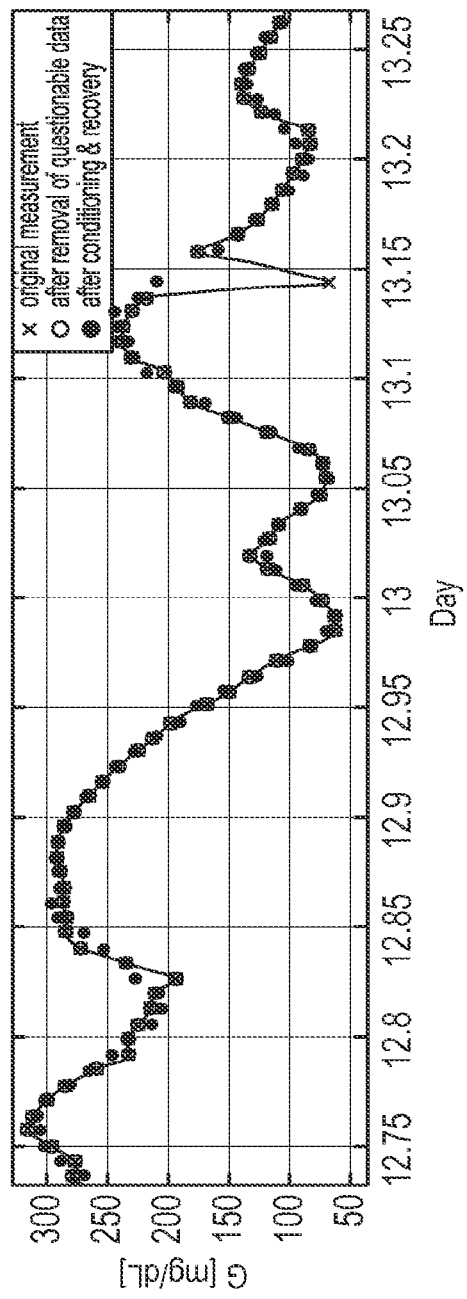
FIG. 5 illustrates sample data analysis to remove questionable data and performing condition and/or data recovery for smooth output in conjunction with the routines above in certain embodiments of the present disclosure.

FIG. 5 illustrates sample data analysis to remove questionable data and performing condition and/or data recovery for smooth output in conjunction with the routines above in certain embodiments of the present disclosure. As shown, sampled glucose data (x) are processed to screen out questionable data. After questionable data are removed, the dataset (circle) goes through the conditioning process described above to obtain the final output values (dots). In this example, the output instances are identical to the measurement instances.

In the manner described above, in certain embodiments of the present disclosure, meal start events and peak events are estimated or determined based on analysis of time series of sampled glucose data from, for example, an in vivo glucose sensor that generates signals corresponding to the monitored glucose level at a specific or programmed or programmable time intervals and which signals can be further processed and analyzed in the manner described above, to estimate meal start and peak events.

In certain embodiments, meal marker manually entered by the user is compared against the estimated meal start determined in accordance with the embodiments of the present disclosure based on sampled glucose data that includes real time data and historical data. A short elapsed time after the meal marker is entered, when the glucose measurements are sufficient to generate a nearby estimate, the user may be prompted (using an analyte monitoring device user interface, for example) to adjust the meal marker timestamp to the estimated instance. In this exemplary embodiment, no estimated meal start replaces user entered marker unless confirmed by the user.

In certain embodiments, retrospective and pseudo-retrospective analysis of time spaced sampled glucose data are performed to generate user viewable reports or analysis results associated with the meal start and peak meal response events estimation, and which are viewable on the user interface of a hand-held data communication device, a mobile telephone screen, a smart phone user interface, or computing device, where the analysis is performed based on collected glucose data acquired up to the current time.

In certain embodiments, data reports are generated based on the meal start event and/or peak meal response events estimated in accordance with the present disclosure, to replace, supplement, revise or confirm such reports that rely on either a) meal tags made by users, b) meal bolus indications from bolus calculators, insulin pumps or smart insulin injection systems, or c) fixed meal times.

In certain embodiments, the meal start event or peak meal response estimation routine in accordance with the present disclosure is used to either cross-check or confirm the absence of presence of meal tags manually entered by the user or a healthcare provider.

In certain embodiments, the meal start event or peak meal response estimation routine in accordance with the present disclosure is used in conjunction with a report or table that is generated from glucose data which is separated into 5 different time-of-day bins defined by fixed meal times and bedtime. The bins may be determined by meal start events based on the meal start event or peak meal response estimation routine in accordance with the present disclosure with predetermined categorization parameters, such as, for example, categorizing identified meal times as a particular meal. For instance, an estimated meal start event would be defined as breakfast if it occurred between 4 am and 10 am.

In certain embodiments, other report designs are contemplated. One example is a report that is used to determine fasting glucose level for diagnosing diabetes. The report algorithm in certain embodiments determine all of the breakfast start times and use a glucose value some time prior to these start values to generate a statistics such as fasting mean and standard deviation. These statistics are compared to thresholds to determine the degree of diabetes condition for the patient or the user. These statistics can also be used to adjust medication therapy—for instance, basal insulin or other medications that address fasting glucose levels.

Reconciling meal tags with the meal detection algorithm in accordance with the embodiments of the present disclosure can also be used to refine the default time of day windows to assist users that have different work and rest schedule, such as someone on a night shift. When the pattern changes (e.g. moves from one work shift to another), the report can be updated to adjust accordingly. However, the moving window-based insight on breakfast (as in the first meal since the longest fast of the day) and other meal times can remain properly grouped in spite of the change in what time of day the meals are ingested.

In certain embodiments, data report may be related to the glucose tolerance test. Typically, a glucose tolerance test is administered by measuring the glycemic response to a 75 gram CHO solution administered orally after fasting. This report would rather utilize a number of days of continuous data and determine the statistics that characterize the glycemic response to typical meals for the patient. Statistics may include mean peak glucose deviation and mean time of peak glucose. These statistics are generated based on data segments aligned by the estimated meal start times. These statistics can be compared to thresholds to determine the degree of diabetes condition for the patient. These statistics can also be used to adjust medication therapy—for instance, mean peak glucose deviation may be used to direct changes to meal-time insulin, and mean time of peak glucose could be used to adjust insulin response time settings or to adjust bolus timing.

In certain embodiments, the meal start event and peak meal response event estimation in accordance with the present disclosure provides meal times that can be used to confirm tagged meals and to identify missing tags when analyzing the data to determine a glycemic model from the data.

In certain embodiments, for closed loop control, the estimated meal start events or peak meal response (in real-time) can be used to prompt the user to indicate if they started eating without notifying the closed loop control system of the meal.

In certain embodiments, estimation of meal start events in accordance with the present disclosure is used to prompt the user to ask questions about the meal. One example is prompting the user for mealtime insulin and carbohydrate, if the meal detection suspects a meal has started, but no entry has been logged related to insulin or carbohydrate information. In certain embodiments, the estimated meal start event, after a pre-determined time delay (say 15 minutes), can be used to set up a reminder to dose insulin. In another embodiment, if an estimated meal start event is determined within the most recent hour (or two) of the current acquisition of the sampled glucose data, and if the retrospective analysis of past data warrants checking post-meal glucose (e.g. due to post-meal variability), a reminder can be set to prompt the user to verify the glucose level (for example, using a finger stick test) at a pre-determined duration since the last meal start.

In another embodiment, the user may be provided with a reviewable or selectable option on the user interface of the analyte monitoring device menu structure to try to recall meal starts. The user can scroll through the graph or listing of glucose values, overlaid with potential meal start instances estimated in accordance with the routines described above. In certain embodiments, any confirmed estimate may be stored or identified or marked as a meal event.

In yet another embodiment, the user entered meal markers and estimated start and peak pairs determined in accordance with the present disclosure may be reconciled in conjunction with a healthcare provider, when the data is retrospectively evaluated.

The various methods described herein for performing one or more processes also described herein may be embodied as computer programs (e.g., computer executable instructions and data structures) developed using an object oriented programming language that allows the modeling of complex systems with modular objects to create abstractions that are representative of real world, physical objects and their interrelationships. However, any practicable programming language and/or techniques may be used. The software for performing the inventive processes, which may be stored in a memory or storage device of the computer system described herein, may be developed by a person of ordinary skill in the art based upon the present disclosure and may include one or more computer program products. The computer program products may be stored on a computer readable medium such as a server memory, a computer network, the Internet, and/or a computer storage device. Note that in some cases the methods embodied as software may be described herein with respect to a particular order of operation or execution. However, it will be understood by one of ordinary skill that any practicable order of operation or execution is possible and such variations are contemplated by this specification of the present disclosure.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

Certain embodiments of the present disclosure include performing conditioning on a plurality of data points corresponding to monitored analyte level over a first time period, for each data point, determining a time derivative based on the conditioned plurality of data points, determining optima of acceleration based on the determined time derivatives, removing false carbohydrate intake start and peak carbohydrate intake response pairs having an amplitude below a predetermined level, removing carbohydrate intake start candidate from the most current carbohydrate intake peak response candidate, removing unpaired carbohydrate intake start candidates and signal artifact falsely identified as carbohydrate intake start and carbohydrate intake peak response pair, and refining the identified carbohydrate intake start and peak carbohydrate intake response pairs.

In one aspect, performing conditioning on the plurality of data points corresponding to the monitored analyte level of the first time period includes performing sample data analysis on the plurality of data points to remove questionable data and smoothing the plurality of data points.

One aspect includes outputting an indication associated with a carbohydrate intake start event.

In a further aspect, the carbohydrate intake start event includes a meal start event.

Another aspect includes outputting an indication associated with a peak carbohydrate intake response event.

In a further aspect, the peak carbohydrate intake response event includes a peak meal response event.

Certain embodiments of the present disclosure include a user interface component and one or more processors operatively coupled to the user interface component, the one or more processors configured to perform conditioning on a plurality of data points corresponding to monitored analyte level over a first time period, for each data point, to determine a time derivative based on the conditioned plurality of data points, to determine optima of acceleration based on the determined time derivatives, to remove false carbohydrate intake start and peak carbohydrate intake response pairs having an amplitude below a predetermined level, to remove carbohydrate intake start candidate from the most current carbohydrate intake peak response candidate, to remove unpaired carbohydrate intake start candidates and signal artifact falsely identified as carbohydrate intake start and carbohydrate intake peak response pair, and to remove the identified carbohydrate intake start and peak carbohydrate intake response pairs.

In one aspect, the one or more processors configured to perform conditioning on the plurality of data points corresponding to the monitored analyte level of the first time period, is further configured to perform sample data analysis on the plurality of data points to remove questionable data, and to smooth the plurality of data points.

In another aspect, the one or more processors is configured to output an indication associated with a carbohydrate intake start event on the user interface component.

In one aspect, the carbohydrate intake start event includes a meal start event.

In another aspect, the one or more processors is configured to output an indication associated with a peak carbohydrate intake response event on the user interface component.

In another aspect, the peak carbohydrate intake response event includes a peak meal response event.

What is claimed is:

1. A computer-implemented method of determining a second data set of carbohydrate intake start events and carbohydrate peak response events, the method comprising:
   determining time derivatives of a plurality of data points corresponding to a monitored analyte level;
   creating a first data set comprising a plurality of carbohydrate intake start candidates and a plurality of carbohydrate intake peak response candidates based on the determined time derivatives;
   removing one or more false carbohydrate intake start candidates or false carbohydrate peak response candidates from the first data set to create the second data set of carbohydrate intake start events and carbohydrate peak response events; and
   outputting a recommended adjustment to a medication therapy based on the second data set of carbohydrate intake events and carbohydrate peak response events.

2. The method of claim 1, further comprising adjusting the medication therapy based on the second data set of carbohydrate intake start events and carbohydrate peak response events.

3. The method of claim 2, wherein adjusting the medication therapy comprises adjusting a basal delivery rate of an insulin pump.

4. The method of claim 2, wherein adjusting the medication therapy comprises adjusting a bolus dosage level, an insulin response time setting, or a bolus timing setting.

5. The method of claim 1, wherein removing the one or more false carbohydrate intake start candidates or false carbohydrate peak response candidates from the first data set includes removing one or more adjacent candidates of a same type.

6. The method of claim 1, wherein removing the one or more false carbohydrate intake start candidates or false carbohydrate peak response candidates from the first data set includes removing a carbohydrate intake start candidate having a proximity or a level drop relative to an adjacent carbohydrate peak response candidate that is below a predetermined threshold.

7. The method of claim 1, wherein removing the one or more false carbohydrate intake start candidates or false carbohydrate peak response candidates from the first data set includes removing one or more unpaired carbohydrate intake start candidates.

8. The method of claim 1, wherein removing the one or more false carbohydrate intake start candidates or false carbohydrate peak response candidates from the first data set includes removing one or more signal artifacts.

9. The method of claim 1, further comprising removing outlier data from the plurality of data points corresponding to the monitored analyte level, and smoothing the plurality of data points.

10. The method of claim 1, further comprising refining temporal positions of the second data set of carbohydrate intake start events and carbohydrate peak response events.

11. An apparatus, comprising:
a user interface component; and
one or more processors operatively coupled to the user interface component and a non-transitory computer readable memory, wherein the non-transitory computer readable memory is configured to store computer readable instructions that, when executed by the one or more processors, cause the one or more processors to:
- determine time derivatives of a plurality of data points corresponding to a monitored analyte level;
- create a first data set comprising a plurality of carbohydrate intake start candidates and a plurality of carbohydrate intake peak response candidates based on the determined time derivatives;
- remove one or more false carbohydrate intake start candidates or false carbohydrate peak response candidates from the first data set to create a second data set of carbohydrate intake start events and carbohydrate peak response events; and
- output a recommended adjustment to a medication therapy based on the second data set of carbohydrate intake events and carbohydrate peak response events.

12. The apparatus of claim 11, wherein the computer readable instructions, when executed by the one or more processors, further cause the one or more processors to adjust the medication therapy based on the second data set of carbohydrate intake start events and carbohydrate peak response events.

13. The apparatus of claim 11, wherein the computer readable instructions, when executed by the one or more processors, further cause the one or more processors to adjust a basal delivery rate of an insulin pump.

14. The apparatus of claim 11, wherein the computer readable instructions, when executed by the one or more processors, further cause the one or more processors to adjust a bolus dosage level, an insulin response time setting, or a bolus timing setting.

15. The apparatus of claim 11, wherein the one or more false carbohydrate intake start candidates or false carbohydrate peak response candidates includes one or more adjacent candidates of a same type.

16. The apparatus of claim 11, wherein the one or more false carbohydrate intake start candidates or false carbohydrate peak response candidates includes a carbohydrate intake start candidate having a proximity or a level drop relative to an adjacent carbohydrate peak response candidate that is below a predetermined threshold.

17. The apparatus of claim 11, wherein the one or more false carbohydrate intake start candidates or false carbohydrate peak response candidates includes one or more unpaired carbohydrate intake start candidates.

18. The apparatus of claim 11, wherein the one or more false carbohydrate intake start candidates or false carbohydrate peak response candidates includes one or more signal artifacts.

19. The apparatus of claim 11, wherein the computer readable instructions, when executed by the one or more processors, further cause the one or more processors to remove outlier data from the plurality of data points corresponding to the monitored analyte level, and smooth the plurality of data points.

20. The apparatus of claim 11, wherein the computer readable instructions, when executed by the one or more processors, further cause the one or more processors to refine temporal positions of the second data set of carbohydrate intake start events and carbohydrate peak response events.

* * * * *